United States Patent
Jiang

(10) Patent No.: US 11,219,418 B2
(45) Date of Patent: Jan. 11, 2022

(54) CT FOCAL POINT DETERMINATION METHOD AND SYSTEM

(71) Applicant: SHANGHAI UNITED IMAGING HEALTHCARE CO., LTD., Shanghai (CN)

(72) Inventor: Yifeng Jiang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 16/889,766

(22) Filed: Jun. 1, 2020

(65) Prior Publication Data
US 2020/0289066 A1   Sep. 17, 2020

Related U.S. Application Data

(63) Continuation of application No. 15/719,990, filed on Sep. 29, 2017, now Pat. No. 10,667,768, which is a
(Continued)

(51) Int. Cl.
*A61B 6/03* (2006.01)
*G21K 1/02* (2006.01)
*A61B 6/00* (2006.01)

(52) U.S. Cl.
CPC ............ *A61B 6/032* (2013.01); *A61B 6/4021* (2013.01); *A61B 6/4291* (2013.01);
(Continued)

(58) Field of Classification Search
None
See application file for complete search history.

(56) References Cited

U.S. PATENT DOCUMENTS

| 5,657,364 A | 8/1997 | Pfoh |
| 6,175,609 B1 | 1/2001 | Edic et al. |

(Continued)

FOREIGN PATENT DOCUMENTS

| CN | 104027127 A | 9/2014 |
| JP | 2000093418 A * | 4/2000 |

(Continued)

OTHER PUBLICATIONS

The Extended European Search Report in European Application No. 17923841.5 dated Aug. 6, 2020, 7 pages.
(Continued)

*Primary Examiner* — Thomas R Artman
(74) *Attorney, Agent, or Firm* — Metis IP LLC

(57) ABSTRACT

A method for determining a CT focal point includes determining a first intensity of first radiation incident on a first detector unit of a scanner, wherein the scanner may include a non-uniform anti-scatter grid (ASG) and a radiation source, and the non-uniform ASG may be configured according to a first focal point of the radiation source. The method also includes determining a second intensity of second radiation incident on a second detector unit of the scanner, wherein the first radiation and the second radiation are emitted from the radiation source with a second focal point. The method further includes determining a displacement of the second focal point from the first focal point based on the first intensity and the second intensity.

20 Claims, 15 Drawing Sheets

Related U.S. Application Data continuation of application No. PCT/CN2017/099899, filed on Aug. 31, 2017.

(52) U.S. Cl.
CPC .......... *A61B 6/5205* (2013.01); *A61B 6/5258* (2013.01); *A61B 6/5264* (2013.01); *A61B 6/582* (2013.01); *G21K 1/025* (2013.01)

(56) References Cited

U.S. PATENT DOCUMENTS

| | | | |
|---|---|---|---|
| 7,085,345 B2 | 8/2006 | Nukui | |
| 7,564,940 B2 | 7/2009 | Mattson et al. | |
| 8,699,659 B2 | 4/2014 | Ikhlef | |
| 8,976,934 B2 | 3/2015 | Demianovich | |
| 9,134,434 B2* | 9/2015 | Niederlohner | A61B 6/4291 |
| 9,380,987 B2* | 7/2016 | Kojima | A61B 6/5205 |
| 9,782,138 B2 | 10/2017 | Koehler et al. | |
| 10,617,369 B2 | 4/2020 | Du | |
| 10,667,768 B2* | 6/2020 | Jiang | A61B 6/032 |
| 10,779,778 B2* | 9/2020 | Rui | A61B 6/06 |
| 2005/0074087 A1* | 4/2005 | Nukui | A61B 6/06 378/7 |
| 2005/0117707 A1 | 6/2005 | Baier et al. | |
| 2009/0225938 A1 | 9/2009 | Zeitler et al. | |
| 2012/0189101 A1 | 7/2012 | Kaneko | |
| 2012/0300907 A1 | 11/2012 | Wirth | |
| 2012/0328076 A1 | 12/2012 | Ikhlef | |
| 2013/0177130 A1 | 7/2013 | Konno et al. | |
| 2013/0336448 A1 | 12/2013 | Demianovich | |
| 2014/0042333 A1* | 2/2014 | Niederlohner | A61B 6/4233 250/394 |
| 2014/0153691 A1 | 6/2014 | Kurochi et al. | |
| 2014/0321610 A1* | 10/2014 | Ueki | G01T 1/243 378/19 |
| 2015/0182179 A1 | 7/2015 | Edic et al. | |
| 2016/0199019 A1 | 7/2016 | Ruimi et al. | |
| 2018/0317869 A1* | 11/2018 | Rui | A61B 6/585 |
| 2018/0368790 A1 | 12/2018 | Ishitsu et al. | |
| 2019/0059846 A1* | 2/2019 | Jiang | A61B 6/4291 |
| 2020/0289066 A1* | 9/2020 | Jiang | A61B 6/4291 |

FOREIGN PATENT DOCUMENTS

| | | |
|---|---|---|
| KR | 20140056113 A | 5/2014 |
| WO | 2015010913 A1 | 1/2015 |

OTHER PUBLICATIONS

International Search Report in POT/CN2017/099899 dated May 24, 2018, 5 pages.
Written Opinion of the International Searching Authority for PCT/CN2017/099899 dated May 24, 2018, 5 pages.
First Office Action in Chinese Application No. 201810547074.5 dated Apr. 21, 2021, 20 pages.

* cited by examiner

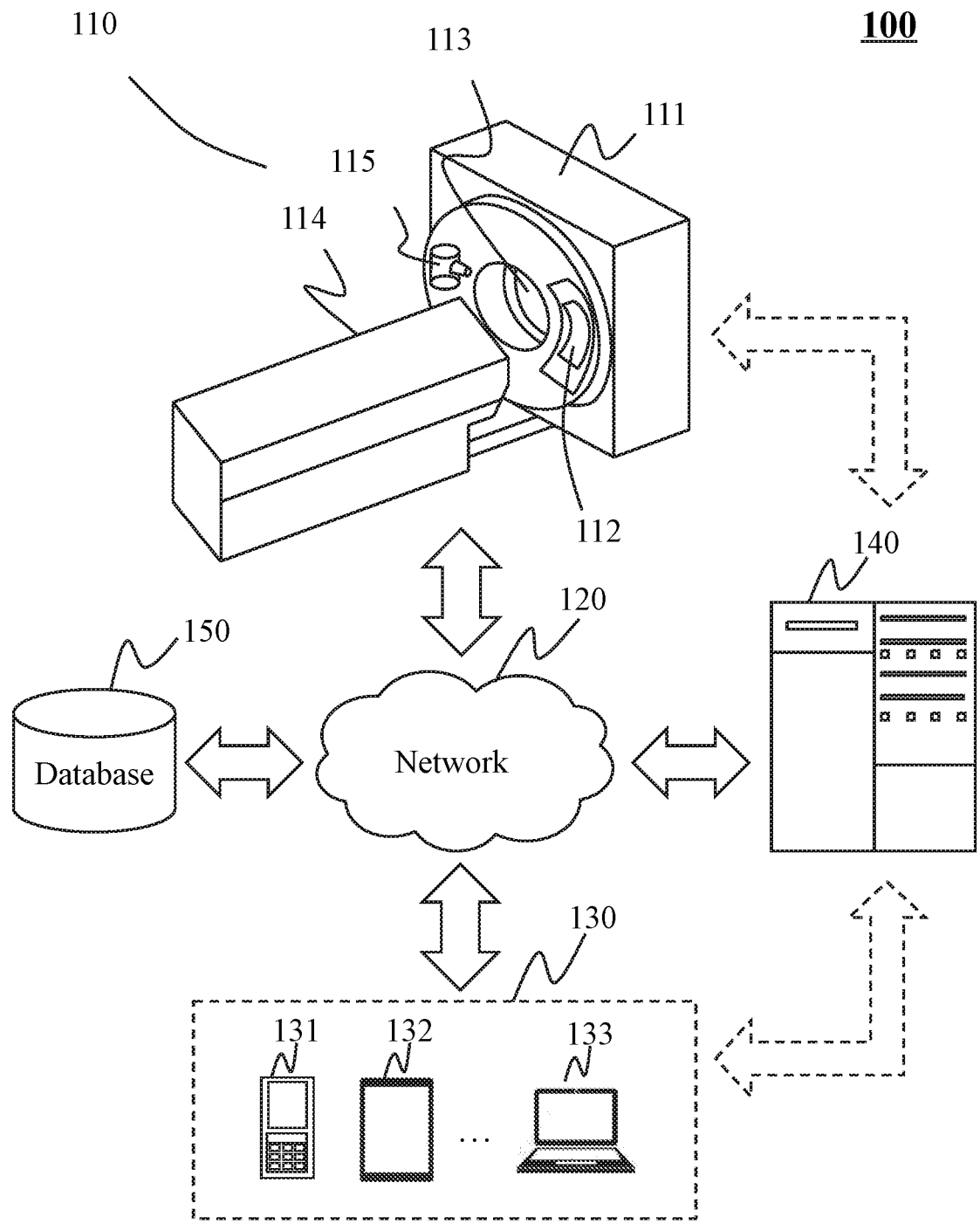
FIG. 1-A

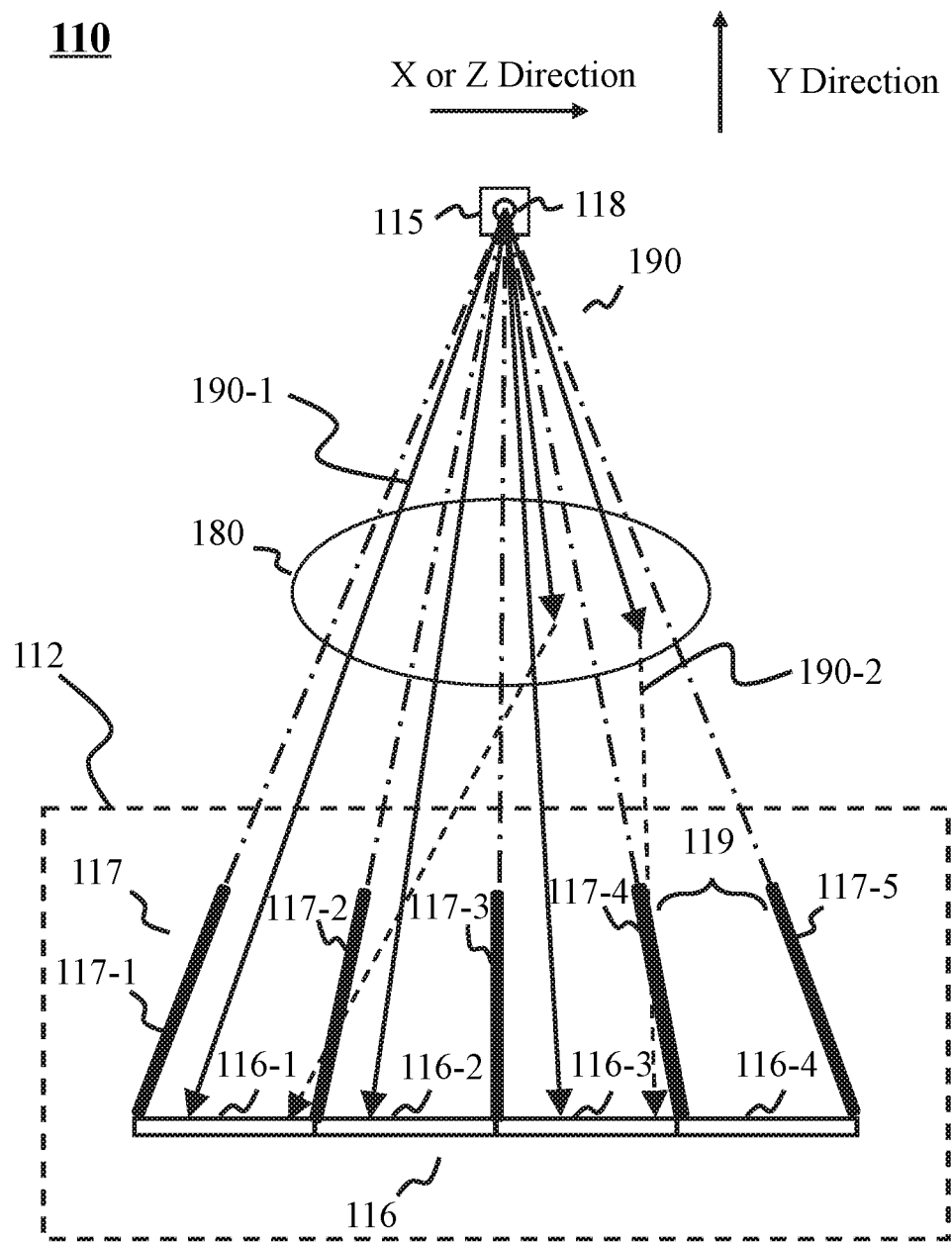
FIG. 1-B

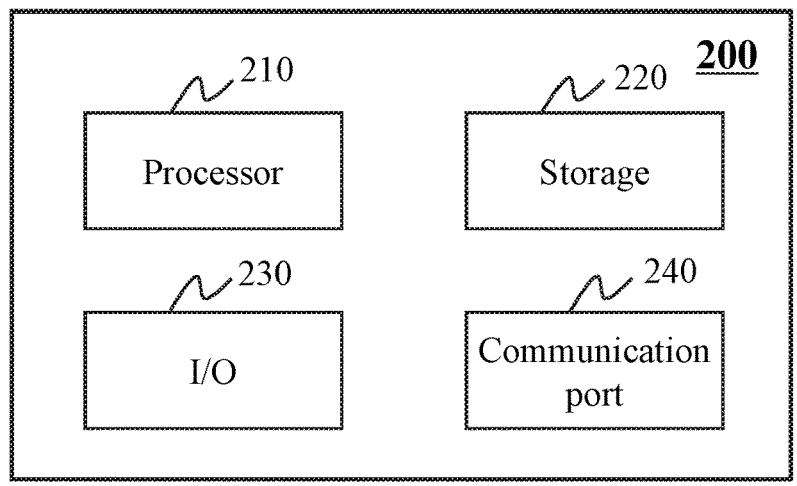
FIG. 2-A
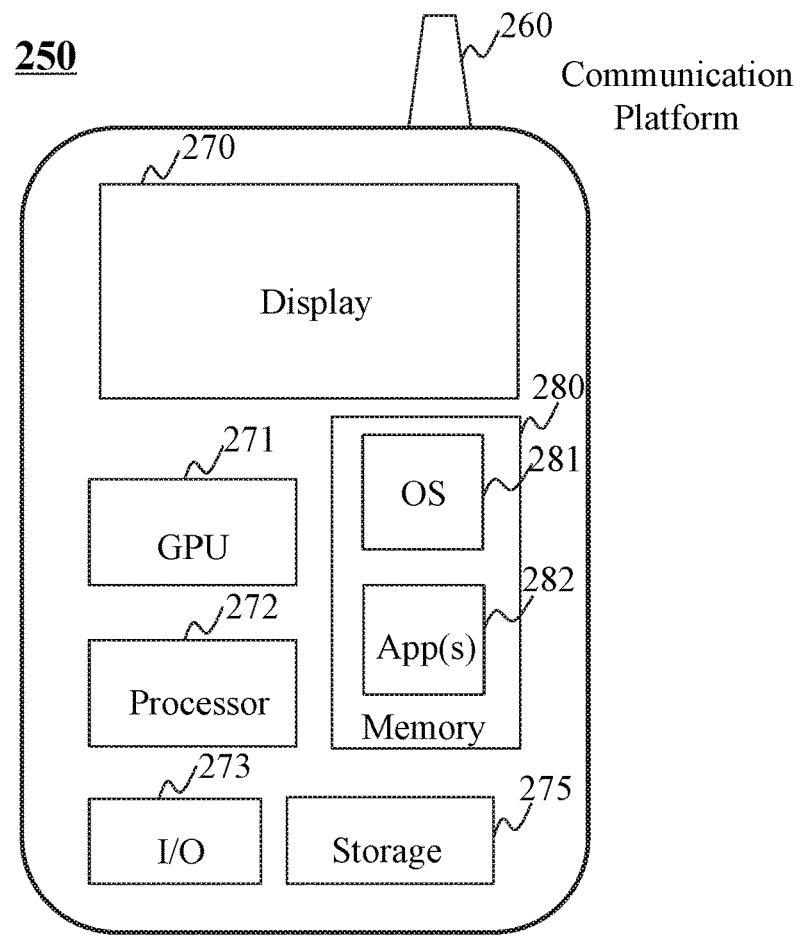
FIG. 2-B

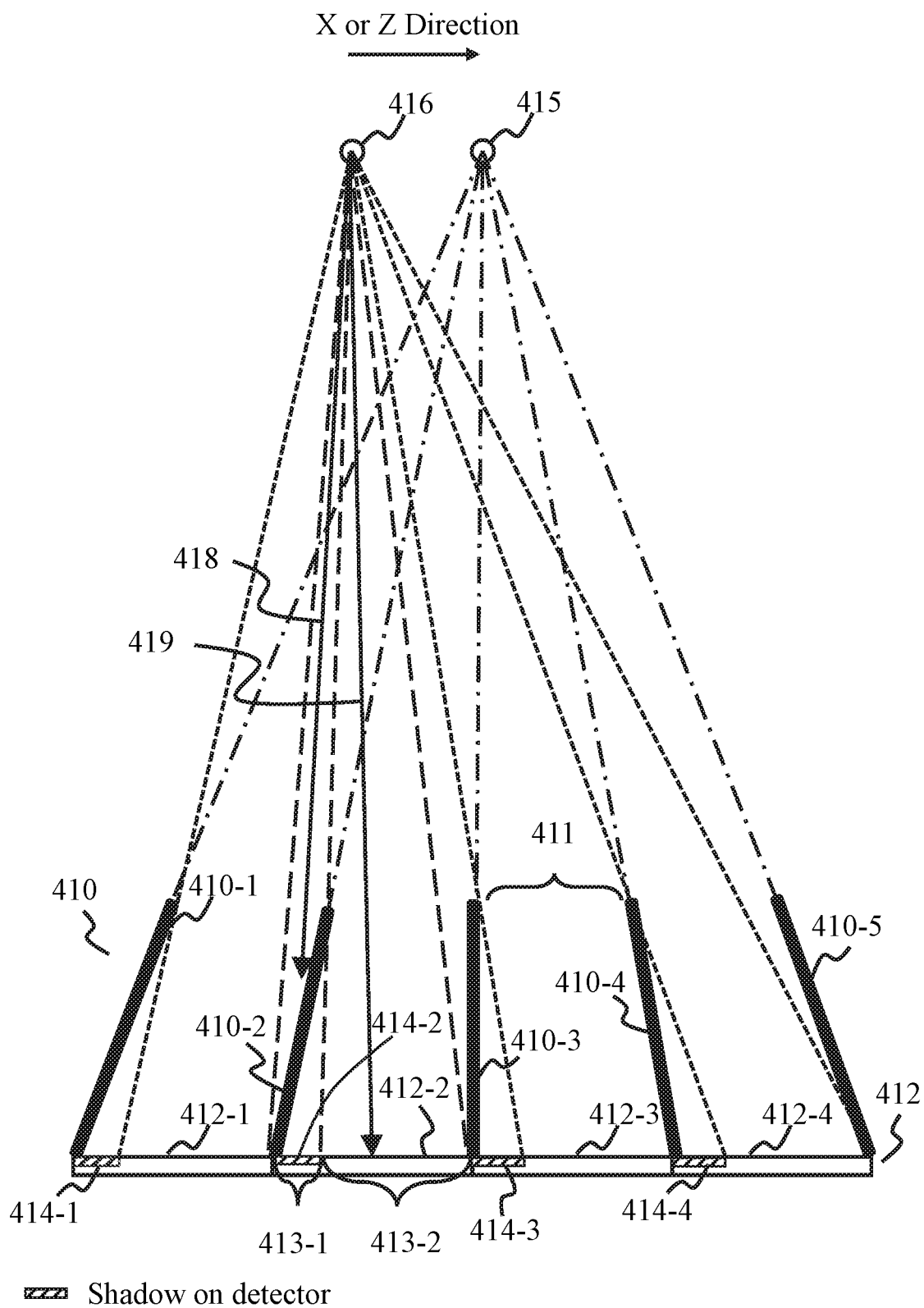
FIG. 4-A

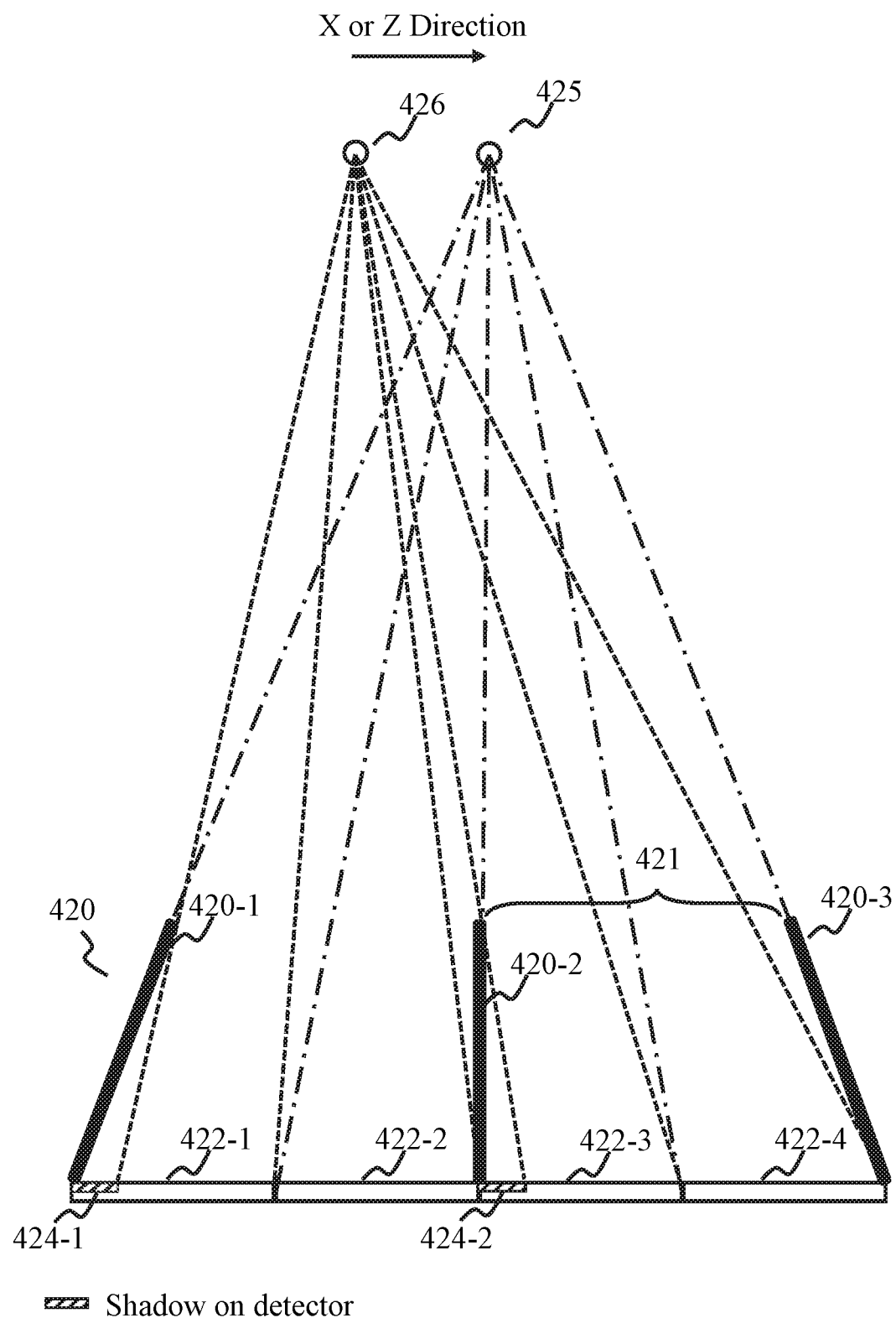
FIG. 4-B

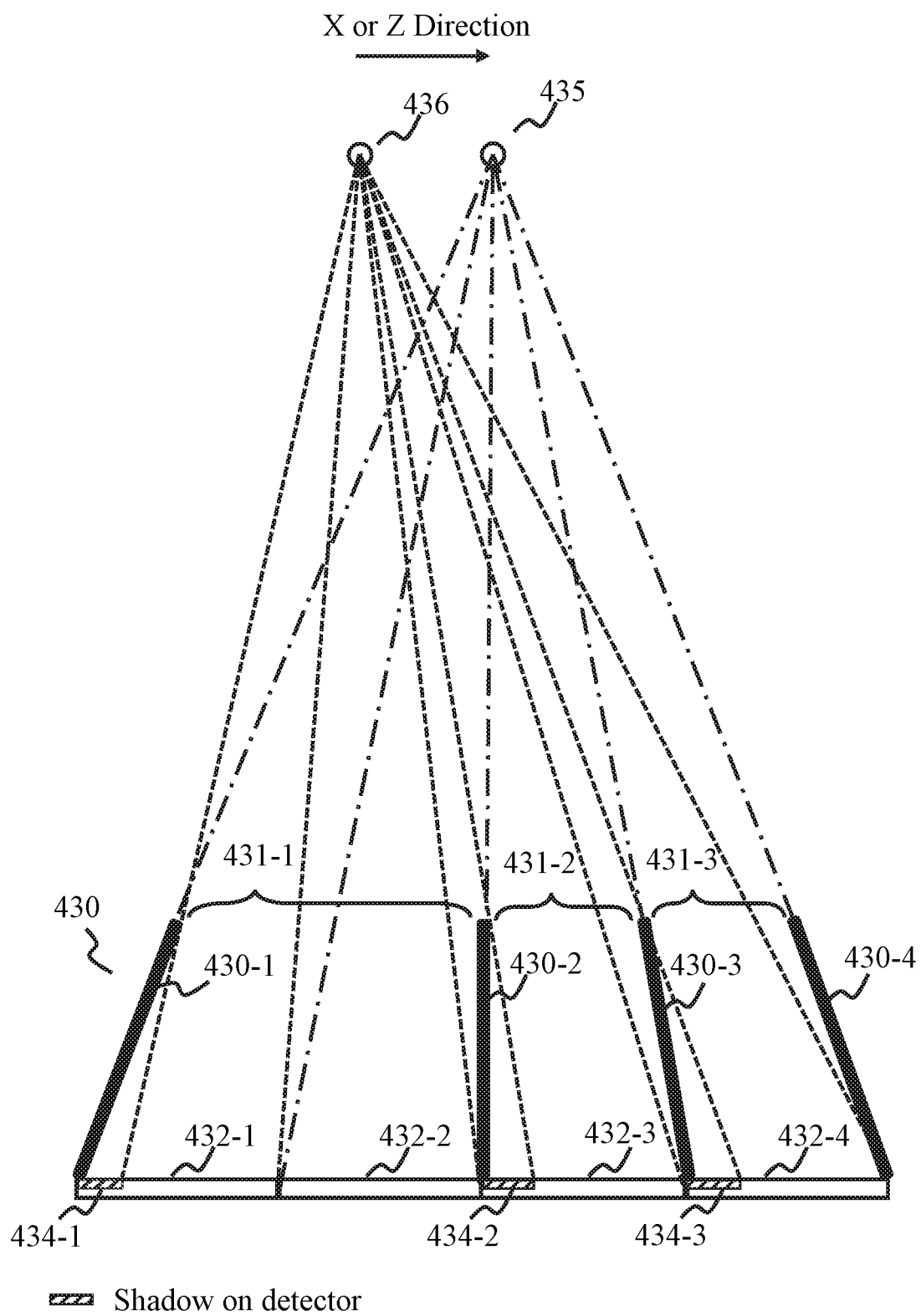
FIG. 4-C

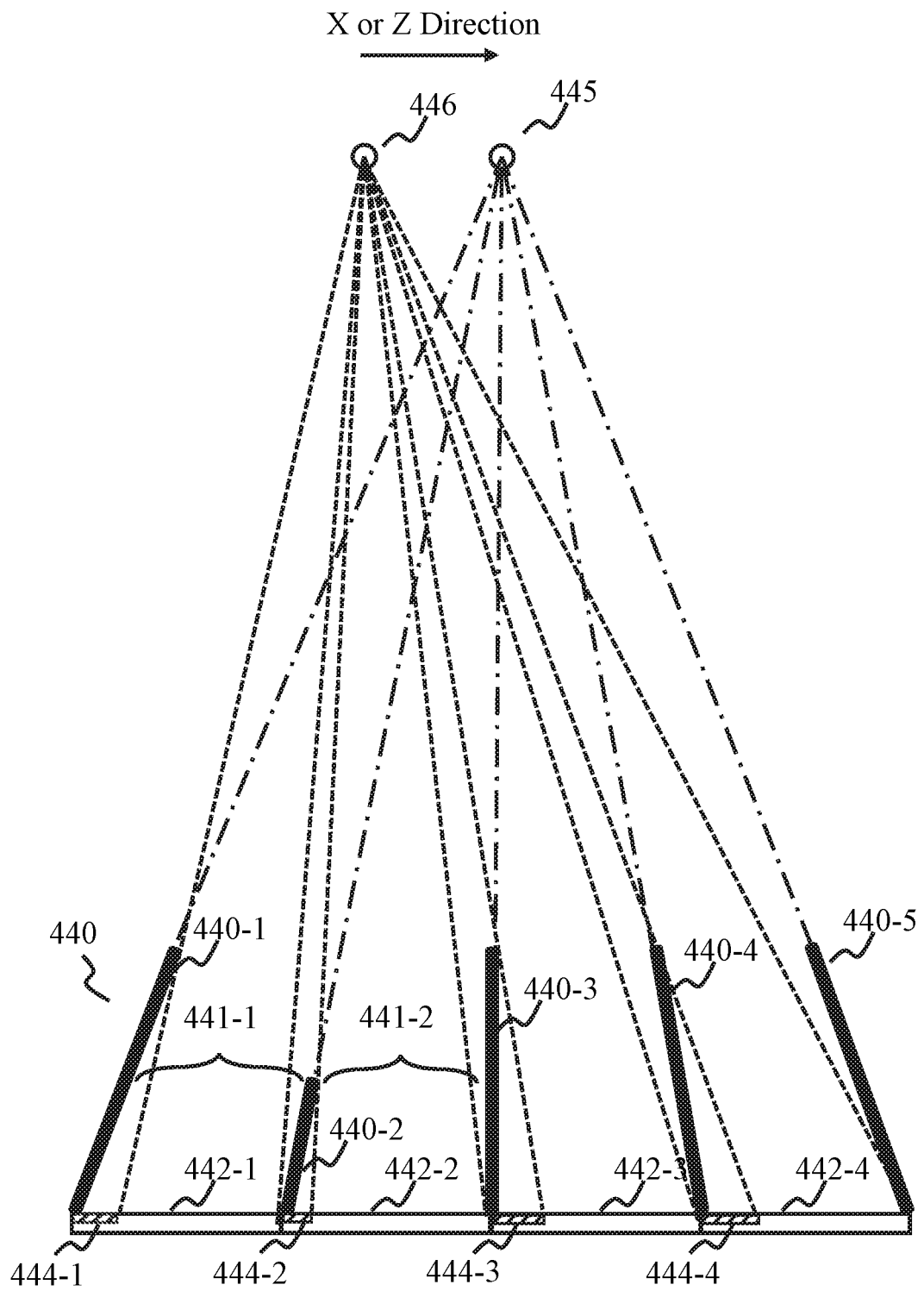
FIG. 4-D

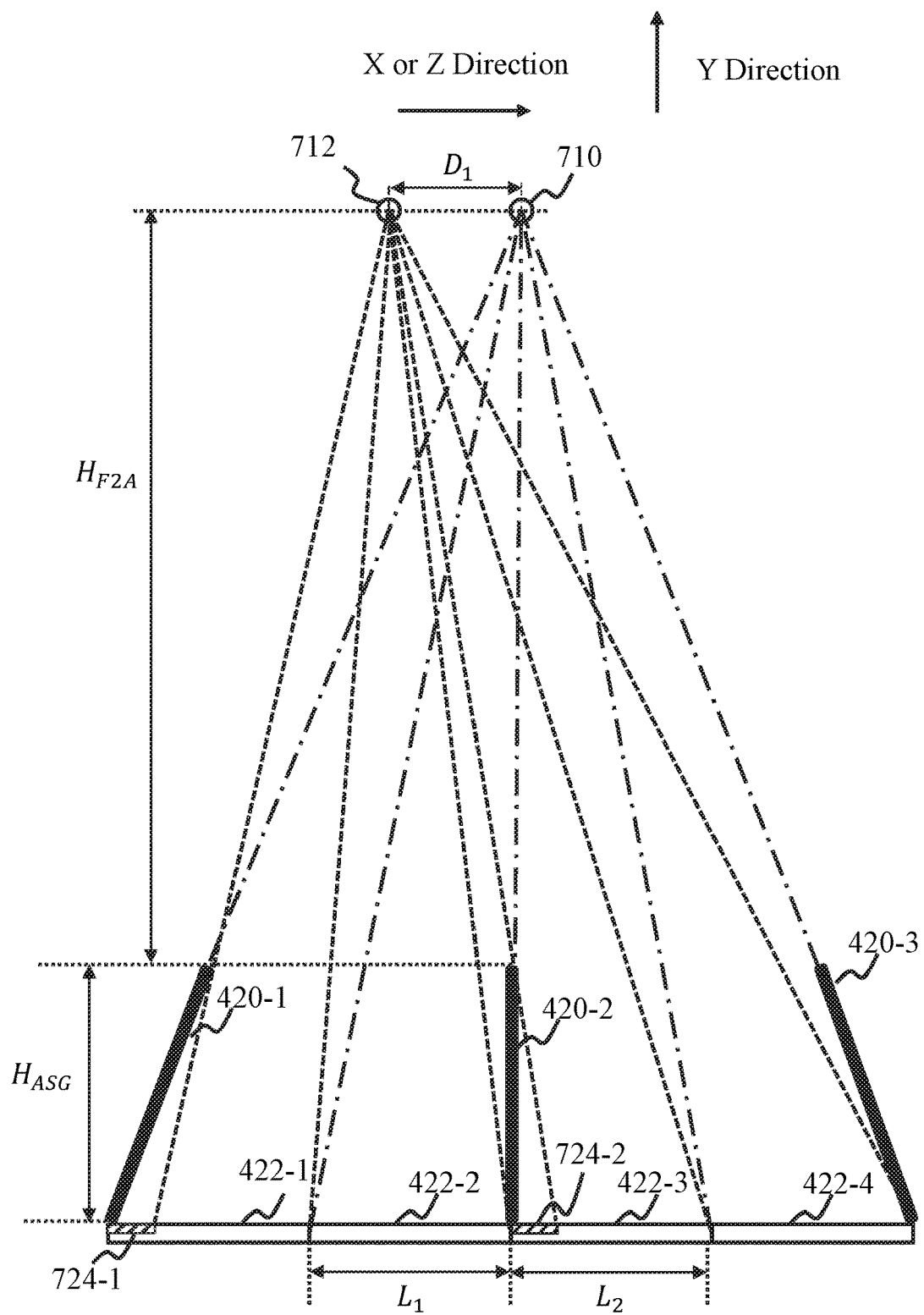
FIG. 7-A

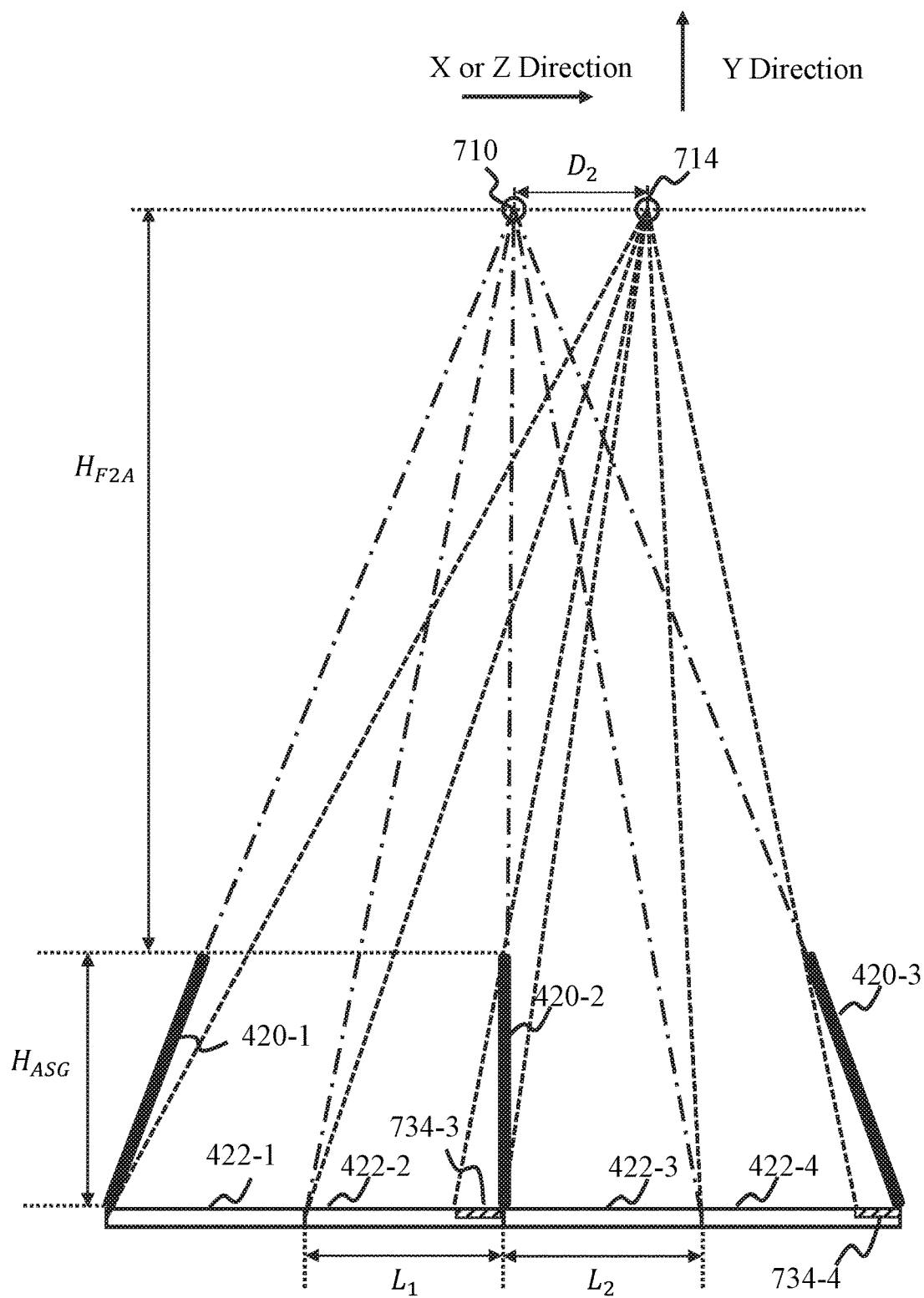
FIG. 7-B

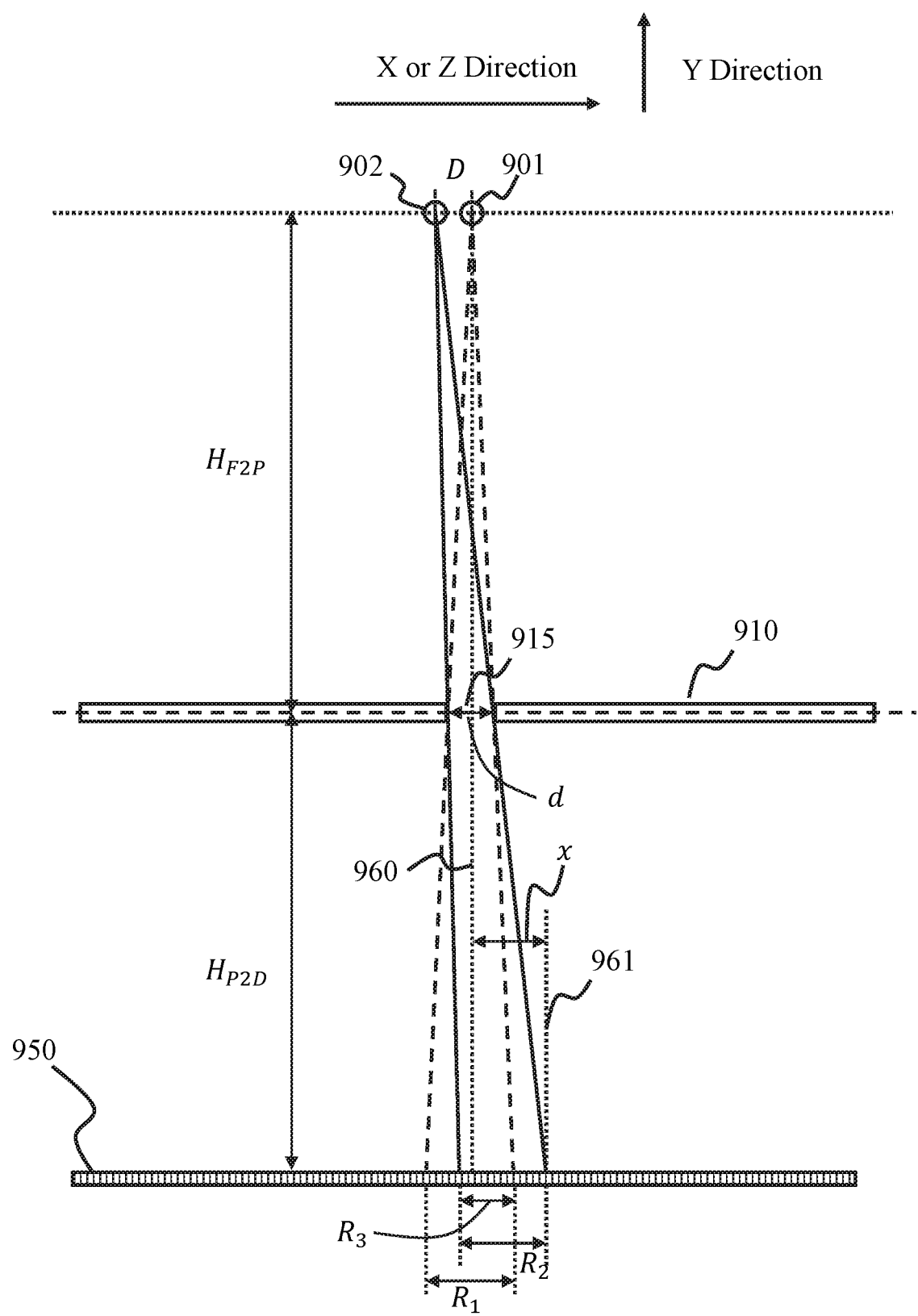
FIG. 9-A

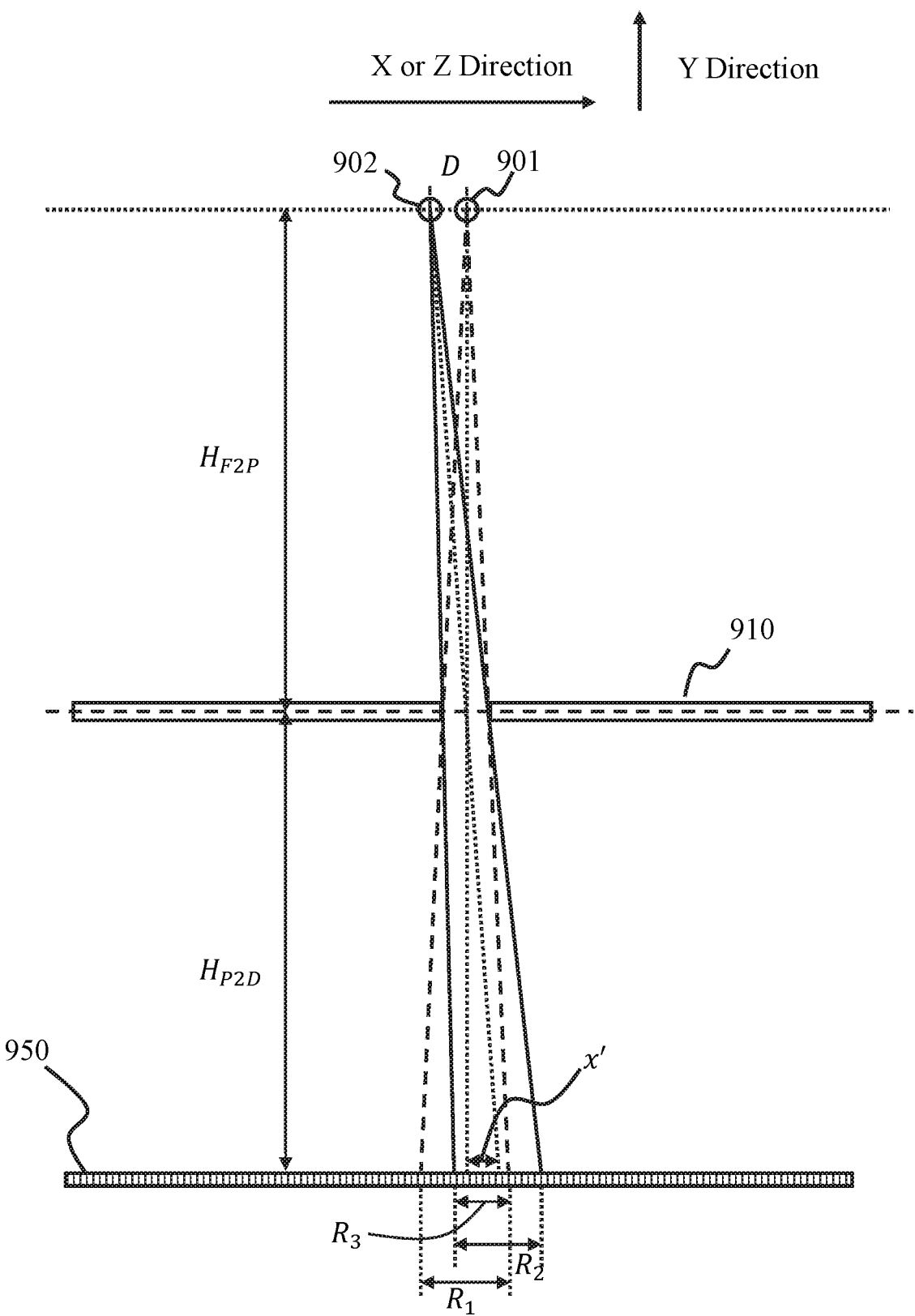
FIG. 9-B

CT FOCAL POINT DETERMINATION METHOD AND SYSTEM

CROSS-REFERENCE TO RELATED APPLICATIONS

This application is a continuation of U.S. application Ser. No. 15/719,990 filed on Sep. 29, 2017, which is a continuation of International Application No. PCT/CN2017/099899 filed on Aug. 31, 2017, the entire contents of which are incorporated herein by reference.

FIELD

The present disclosure generally relates to a technical field of a CT scanner, and more particularly to a focal point determining method and system for determining the focal point of a radiation source of a CT scanner.

BACKGROUND

During a scanning performed by a computed tomography (CT) scanner equipped with anti-scatter grids (ASGs), the displacement of the focal point of the radiation source of the CT scanner may cause a portion of the radiation emitted by the radiation source intended to be received by the detector of the CT scanner blocked by the ASGs, causing a reduction of the quality of the image generated based on the scanning. Various hardware related (e.g., focus point tracing) or software related (e.g., image post-processing) techniques may be adopted for compensating the image quality reduction. However, the displacement of the focal point needs to be determined for most of these techniques. There is a need for a method of low cost and high reliability for determining the displacement of the focal point during the scanning of the CT scanner.

SUMMARY

According to an aspect of the present disclosure, a method may include determining a first intensity of first radiation incident on a first detector unit of a scanner. The scanner may include a non-uniform anti-scatter grids (ASG) and a radiation source, and the non-uniform ASG may be configured according to a first focal point of the radiation source. The method may also include determining a second intensity of second radiation incident on a second detector unit of the scanner, wherein the first radiation and the second radiation are emitted from the radiation source with a second focal point. The method may further include determining a displacement of the second focal point from the first focal point based on the first intensity and the second intensity.

In some embodiments, the determining the displacement may comprise determining a ratio of the first intensity to the second intensity; and determining the displacement based on the ration.

In some embodiments, the method may further comprising determining a correlation between the displacement and the ratio using a pinhole positioned between the radiation source and a detector of the scanner, the detector including the first detector unit and the second detector unit, wherein the displacement is determined further based on the correlation In some embodiments, the method may further include generating, based on the displacement, a calibration instruction for calibrating the scanner.

In some embodiments, the method may further include obtaining scan data by controlling the scanner to scan a subject, and generating an image based on the scan data and the displacement.

In some embodiments, the first radiation and the second radiation may be emitted during the obtaining the scan data.

In some embodiments, the non-uniform ASG may include at least one first cell. The first detector unit and the second detector unit may be included in the first cell.

In some embodiments, the non-uniform ASG may include at least one second cell and at least one third cell having different structures. The second cell and the third cell may include plates of different heights. The first detector unit may be included in the second cell, and the second detector unit may be included in the third cell.

In some embodiments, the method may further include obtaining at least one parameter relating to the non-uniform ASG, wherein the displacement is determined based at least in part on the at least one parameter.

In some embodiments, the at least one parameter may comprise at least one of a height of at least a portion of the non-uniform ASG and a distance from the second focal point to a top of the at least a portion of the non-uniform ASG.

According to another aspect of the present disclosure, a system may include at least one processor and at least one storage device storing instructions. When executing the instructions, the at least one processor may be configured to cause the system to determine a first intensity of first radiation incident on a first detector unit of a scanner, wherein the scanner may include a non-uniform anti-scatter grids (ASG) and a radiation source, and the non-uniform ASG may be configured according to a first focal point of the radiation source. The at least one processor may also be configured to cause the system to determine a second intensity of second radiation incident on a second detector unit of the scanner, wherein the first radiation and the second radiation may be emitted from the radiation source with a second focal point. The at least one processor may further be configured to cause the system to determine a displacement of the second focal point from the first focal point based on the first intensity and the second intensity.

According to yet another aspect of the present disclosure, an anti-scatter grid for determining a focal point of a radiation source of a scanner may include a plurality of plates defining a plurality of cells. The plurality of cells may include at least one first cell. After the anti-scatter grid being installed on a detector of the scanner, the first cell may include a first detector unit and a second detector unit of the detector.

In some embodiments, the first detector unit and the second detector unit may be adjacent to one another.

In some embodiments, each of the plurality of cells of the anti-scatter grid have a same configuration as the first cell.

According to yet another aspect of the present disclosure, an anti-scatter grid for determining a focal point of a radiation source of a scanner may include a plurality of plates defining a plurality of cells. The plurality of cells may include at least one second cell and at least one third cell. The second cell and the third cell may include plates of different heights. The second cell and the third cell may have different structures. After the anti-scatter grid being installed on a detector of the scanner, the second cell may include a first detector unit of the detector, and the third cell may include a second detector unit of the detector.

In some embodiments, the second cell and the third cell may be adjacent to one another.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTIONS OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1-A is a schematic diagram illustrating an exemplary CT system according to some embodiments of the present disclosure;

FIG. 1-B is a schematic diagram illustrating an exemplary structure and mechanism of a CT scanner according to some embodiments of the present disclosure;

FIG. 2-A is a schematic diagram illustrating exemplary hardware and/or software components of an exemplary computing device on which the processing engine may be implemented according to some embodiments of the present disclosure;

FIG. 2-B is a schematic diagram illustrating exemplary hardware and/or software components of an exemplary mobile device on which the terminal may be implemented according to some embodiments of the present disclosure;

FIG. 3 is a schematic diagram illustrating an exemplary processing engine according to some embodiments of the present disclosure;

FIG. 4-A is a schematic diagram illustrating the effect of the change of the focal point of the radiation source in the CT scanner;

FIGS. 4-B, 4-C and 4-D are schematic diagrams illustrating exemplary non-uniform ASGs according to some embodiments of the present disclosure;

Figure 6:
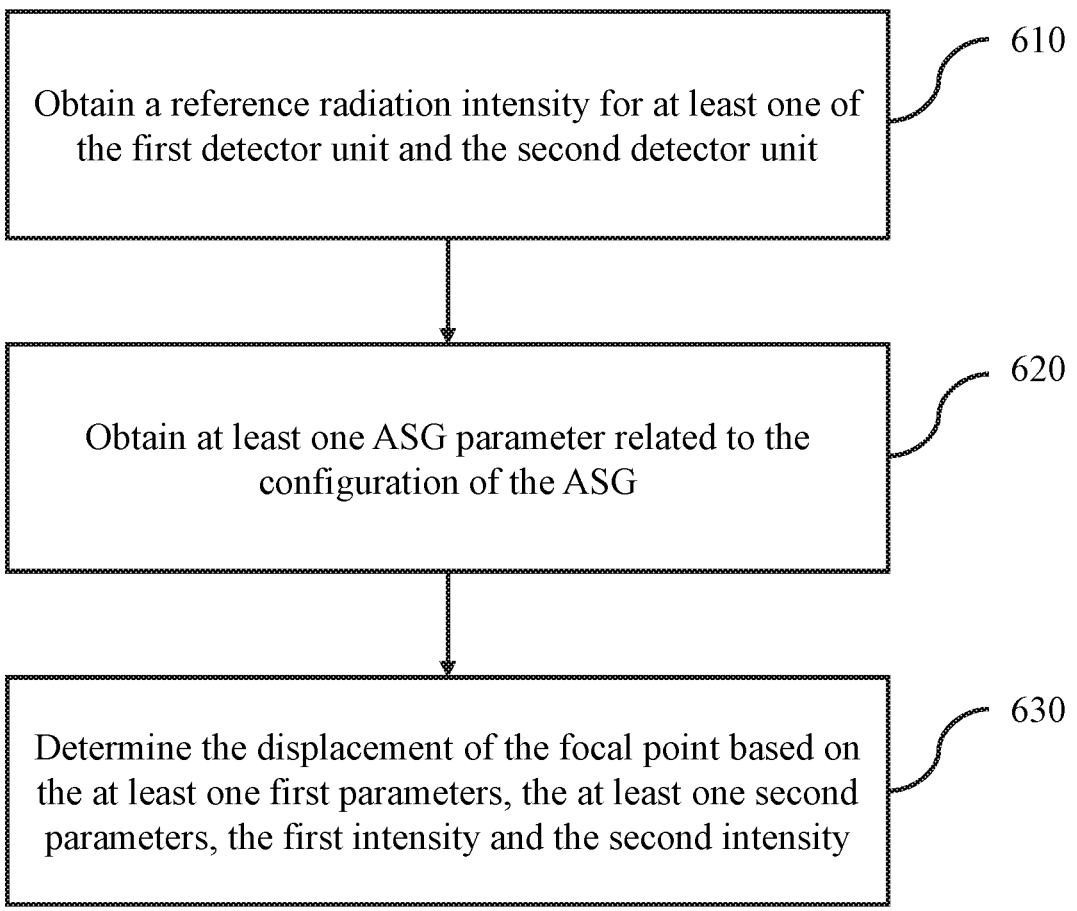
FIG. 6 is a schematic diagram illustrating an exemplary process for determining the displacement of the focal point based on the first intensity and the second intensity according to some embodiments of the present disclosure.
Figure 8:
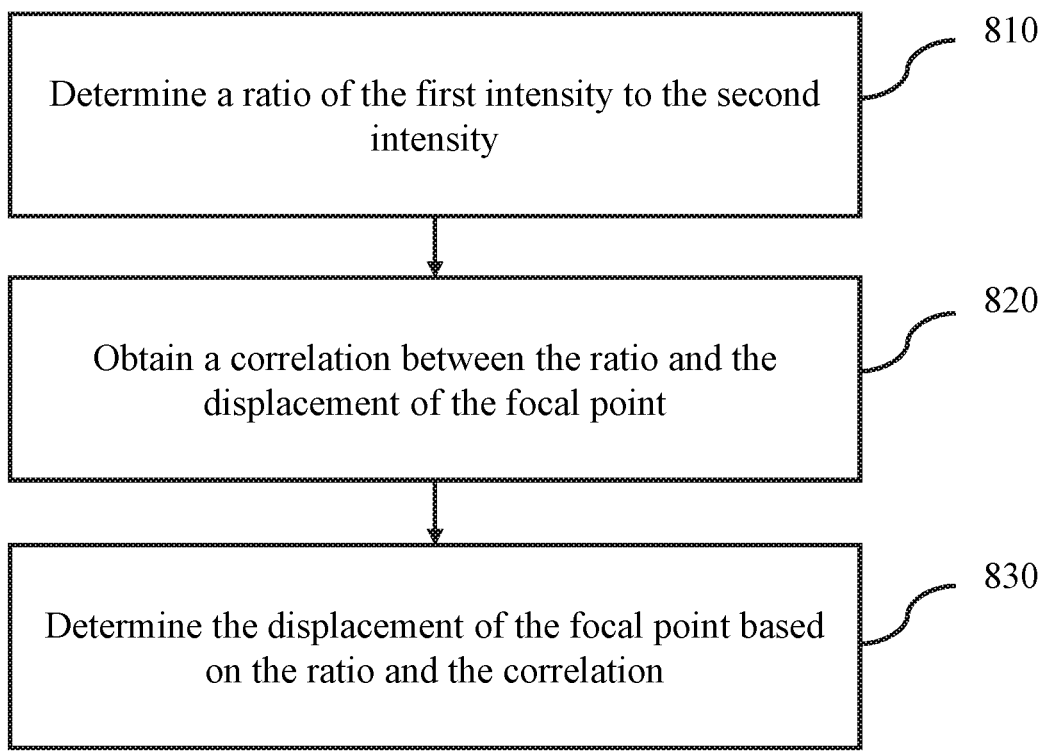

FIGS. 7-A and 7-B are schematic diagrams of the process illustrated in FIG. 6 according to some embodiments of the present disclosure;

FIG. 8 is a schematic diagram illustrating an exemplary process for determining the displacement of the focal point based on the first intensity and the second intensity according to some embodiments of the present disclosure;

FIGS. 9-A and 9-B are schematic diagrams illustrating exemplary techniques for generating the correlation between the ratio of the first intensity to the second intensity and the displacement of the focal point according to some embodiments of the present disclosure.

DETAILED DESCRIPTION

The present disclosure is directed to determine a focal point of the radiation source of a CT scanner equipped with a non-uniform ASG during the scanning performed by the CT scanner.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a", "an", and "the" may be intended to include the plural forms as well, unless the context clearly indicates otherwise. It will be further understood that the terms "comprise", "comprises", and/or "comprising", "include", "includes", and/or "including", when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by other expression if they achieve the same purpose.

Generally, the word "module," "sub-module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2-A) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure.

FIG. 1-A is a schematic diagram illustrating an exemplary CT system according to some embodiments of the present disclosure. As shown, CT system 100 may include a CT scanner 110, a network 120, one or more terminals 130, a processing engine 140, and a storage 150.

The CT scanner 110 may include a gantry 111, a detector 112, a detecting region 113, a table 114, and a radiation source 115. The gantry 111 may support the detector 112 and the radiation source 115. A subject may be placed on the table 114 for scanning. The radiation source 115 may emit radiation beams (e.g., X-rays) to the subject. The detector 112 may detect the radiation beams penetrated through at least part of the subject within the detection region 113. In some embodiments, the CT scanner 110 may also be part of a multi-modality system including, for example, PET-CT, SPECT-CT, etc. In some embodiments, a more detailed structure and mechanism of the CT scanner 110 is illustrated in FIG. 1-B. In some embodiments, one or components in the CT system 100 may be omitted. Merely by way of example, the CT system 100 may not include the terminal(s) 130.

The connection between the components in the CT system 100 may be variable. Merely by way of example, as illustrated in FIG. 1-A, the CT scanner 110 may be connected to the processing engine 140 through the network 120. As another example, the CT scanner 110 may be connected to the processing engine 140 directly as illustrated by the dotted double arrow between the CT scanner 110 and the processing engine 140. As a further example, a terminal 130 may be connected to other portions of the system 100 through the network 120. As still a further example, the CT scanner 110 may be connected to a portion of the system 100, e.g., the processing engine 140 directly as illustrated by the dotted double arrow between the processing engine 140 and a terminal 130.

For demonstration purposes, a coordinate system as shown in FIG. 1-A may be used to describe direction related issues in the present disclosure.

The network 120 may include any suitable network that can facilitate exchange of information and/or data for the CT system 100. In some embodiments, one or more components of the CT system 100 (e.g., the CT scanner 110, the terminal 130, the processing engine 140, the storage 150) may communicate information and/or data with one or more other components of the CT system 100 via the network 120. For example, the processing engine 140 may obtain image data from the CT scanner 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the CT system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

The processing engine 140 may process data and/or information obtained from the CT scanner 110, the terminal 130, and/or the storage 150. For example, the processing engine 140 may generate an image based on data relating to an object obtained from the CT scanner 110. The data relating to the object may include projection data corresponding to radiation beams traversing the object. The image may be generated by using an analytical algorithm, an iterative algorithm, and/or other reconstruction techniques. In some embodiments, the processing engine 140 may include a digital-analog converter (DAC) which may convert the image data into an analog signal. The analog signal may be processed and transmitted to the terminal 130 for display.

The processing engine 140 may also determine the focal point or the displacement of the focal point of the radiation source 115 of the CT scanner 110. The processing engine 140 may further use the obtained focal point or the displacement of the focal point to calibrate the CT scanner 110 or process the image generated based on the data obtained from the CT scanner 110. Detailed descriptions of the processing engine 140 are provided elsewhere in the present disclosure (e.g., in connection with FIG. 3).

In some embodiments, the processing engine 140 may be a computer, a user console, a single server or a server group, etc. The server group may be centralized or distributed. In some embodiments, the processing engine 140 may be local or remote. For example, the processing engine 140 may access information and/or data stored in the CT scanner 110, the terminal 130, and/or the storage 150 via the network 120. As another example, the processing engine 140 may be directly connected to the CT scanner 110, the terminal 130 and/or the storage 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components as illustrated in FIG. 2-A.

The storage 150 may store data, instructions, and/or any other information. In some embodiments, the storage 150 may store data obtained from the terminal 130 and/or the processing engine 140. In some embodiments, the storage 150 may store data and/or instructions that the processing engine 140 may execute or use to perform exemplary methods described in the present disclosure. In some embodiments, the storage 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the CT system 100 (e.g., the processing engine 140, the terminal 130). One or more components in the CT system 100 may access the data or instructions stored in the storage 150 via the network 120. In some embodiments, the storage 150 may be directly connected to or communicate with one or more other components in the CT system 100 (e.g., the processing engine 140, the terminal 130). In some embodiments, the storage 150 may be part of the processing engine 140.

FIG. 1-B is a schematic diagram illustrating an exemplary structure and mechanism of a CT scanner according to some embodiments of the present disclosure. FIG. 1-B is a sectional view of the CT scanner 110 along the Z axis or the X axis within the detection region 113. The radiation source 115 may emit radiation beams 190. The radiation beams 190 may penetrate an object 180 (e.g., a body, an organ, a tissue, a container) and reach the detector 112. The detector 112 may include a plurality of detector units 116 (e.g., detector units 116-1~116-4). In response to the incident radiation beams, the plurality of detector units 116 may generate signals that may be used for generating an image of the object 180. The CT scanner 110 may then transmit the signals to the network 120, the processing engine 140, and/or other components of the CT system 100.

The radiation source 115 may include a tube, such as a cold cathode ion tube, a high vacuum hot cathode tube, a rotating anode tube, etc. The tube may be powered by a high voltage generator for emitting the radiation beams 190. The radiation beams 190 may be and/or include a particle ray, a photon ray, or the like, or a combination thereof. The radiation source 115 may be viewed as a point for approximation. The radiation beams 190 may also be considered as being emitted from this point. The point defined by the radiation source 115 may be referred to as a focal point (e.g., focal point 118). In the present disclosure, the term "focal point" may also relate to the location of the point.

The radiation beams 190 emitted by the radiation source 115 may include, for example, a plurality of primary radiation beams (e.g., radiation beam 190-1) and a plurality of scattered radiation beams (e.g., radiation beam 190-2). The primary radiation beams may propagate along a trajectory path from the focal point 118 to the detector 112. The trajectory path may be, for example, a straight connection between the focal point 118 and the incident point at the corresponding detector unit 116. The scattered radiation beams may include radiation beams emitted by the radiation source 115 that are scattered or deflected while penetrating the object 180. The scattered radiation beams may deviate from their original paths (e.g., trajectory paths). A primary radiation beam may be one that may contribute to the generation of desired imaging data for generating an image of the object 180. A scattered radiation beam, when detected by a detector unit, may cause artifacts in the image of the object 180.

In some embodiments, for reducing the artifacts in the image of the object 180, the detector 112 may further include one or more anti-scatter grids (ASGs, e.g., ASG 117) for limiting the scattered radiation beams received by the detector units 116. The ASG 117 may include a plurality of plates (e.g., plates 117-1~117-5). The plates may include materials that can absorb one or more types of radiation. The radiation absorbing material may include, for example, tungsten, lead, uranium, gold, silver, copper, molybdenum, or the like, or a combination thereof. The interspaces (or cells) enclosed by the plates may be filled with air or a radiolucent material. Exemplary radiolucent materials may include, for example, plastic, carbon fiber, aluminum, inorganic non-metallic material (e.g., paper, ceramic), or the like, or a combination thereof. The ASG 117 may allow the radiation beams passing through the cells (e.g., cell 119) defined by the plates to be received by the detector units 116 (e.g., detector units 116-1~116-4). The ASG 117 may block (or absorb) at least a majority of the radiation beams hitting the plates of the ASG 117.

The ASG 117 may be installed or placed between the radiation source 115 and detector units 116. The plates of the ASG 117 may be aligned toward the focal point 118 and be distributed along the X direction and/or Z direction. The primary radiation beams (e.g., radiation beam 190-1) emitted from the focal point 118 may pass through the ASG 117 and be received by the detector units 116. The scattered radiation beams (or at least some of them, e.g., radiation beam 190-2), as deviated from their original paths, may hit the plates of the ASG 117 and be absorbed by the ASG 117. The scattered radiation beams may then be attenuated, or removed, from the plurality of radiation beams.

In the present disclosure, the X direction and the Z direction, which are perpendicular to each other, are set parallel with the detector 112 or the tangent plane of the center of the detector 112. The X direction and the Z direction are also set parallel with the axis of the detection region 113. The Y direction (not shown in FIG. 1-B) is perpendicular to both the X direction and the Z direction.

In the present disclosure, for the determination of the focal point of the radiation source 118, one or more ASGs installed on the CT scanner 110 may be non-uniform ASGs. As one aspect, the term "non-uniform ASG" may indicate that the ASG has non-uniformly arranged plates. For instance, at least two of the plates of the non-uniform ASG may have different shapes, sizes (e.g., heights), and/or be made of different materials (e.g., with different radiation absorbance), etc. The non-uniform ASG of this type may be referred to as Type I non-uniform ASG. FIGS. 4-C and 4-D are schematic diagrams illustrating Type I non-uniform ASGs according to this aspect.

Alternatively or additionally, the term "non-uniform" may indicate that the ASG has a structure different from that of a majority of (e.g., more than 50%) the other ASGs installed on the CT scanner 110. The "non-uniform" ASG itself may have uniformly (e.g., as illustrated in FIG. 4-B) or non-uniformly (e.g., as illustrated in FIGS. 4-C and 4-D) arranged plates. The majority of the other ASGs may share a same structure. Merely for example, the cells of the majority of the other ASGs may each include one detector unit in one direction (e.g., the X direction, the Z direction), while the cells of the non-uniform ASG(s) may each include two or more detector units in the same direction. The non-uniform ASG of this type may be referred to as type II non-uniform ASG.

In some embodiments, the one or more non-uniform ASGs installed on the CT scanner 110 may only be type I non-uniform ASGs. For instance, all the ASGs (or the only one ASG) installed on the CT scanner 110 may be the same type I non-uniform ASGs (e.g., ASGs as illustrated in FIGS. 4-C and 4-D).

In some embodiments, the one or more non-uniform ASGs installed on the CT scanner 110 may only be type II non-uniform ASGs. The type II non-uniform ASGs may share a same structure or have different structures.

In some embodiments, the one or more non-uniform ASGs installed on the CT scanner 110 may be both the type I and type II non-uniform ASGs. These non-uniform ASGs may share a same structure or have different structures.

A detector unit 116 may detect radiation beams penetrating the object 180 and then passing through the ASG 117 (if any). The detector unit 116 may also be referred to as a detector element or a detector pixel. The detector unit 116 may convert the incident radiation beams into a signal. The amplitude of the generated signals may correlate with the intensities of the radiation reaching the detector unit 116. The detector unit 116 may include a scintillator and/or a photoelectric sensor, etc. Exemplary materials of the detector unit 116 may include an inert gas (e.g., Xe), CdWO4, Gd2O2S (GOS), or ceramic (e.g., HiLight™), or the like, or a combination thereof.

The detector units 116 may be arranged in a single row or multiple rows. For illustration purposes, FIG. 1-B only illustrates one row. The detector units 116 may be arranged on a flat plane (as shown in FIG. 1-B) or a curved plane (not shown). In some embodiments, the detector units 116 may be aligned with their normal directions pointing at the focal point 118.

When the ASG(s) is installed on the detector 116, one or more detector units may be positioned inside a cell of the ASG. A non-uniform ASG (type I and/or type II) may cover an arbitrary portion of the detector 116. Merely for example, the installed non-uniform ASG(s) may cover the whole detector 116, the central part of the detector 116, and/or the edge part of the detector 116.

It may be noted that, FIG. 1-B is only provided for demonstration purposes, and is not intend to apply a limitation to the present disclosure. Modification and amendment may be made to FIG. 1-B. The numbers, appearances, and relative locations of the components (e.g., the plates of the ASG 117, the detector units, the radiation beams) of the CT scanner 110 are also for illustration and may not reflect their true states in practical use.

FIG. 2-A is a schematic diagram illustrating exemplary hardware and/or software components of an exemplary computing device on which the processing engine may be implemented according to some embodiments of the present disclosure. As illustrated in FIG. 2-A, the computing device 200 may include a processor 210, a storage 220, an input/output (I/O) 230, and a communication port 240.

The processor 210 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 210 may be configured to perform the functions relating to the determination of the focal point or the displacement of the focal point of the radiation source 115 of the CT scanner 110.

In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus steps and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the scanner 110, the terminal 130, the storage 150, and/or any other component of the imaging system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 140 for determining a regularization item.

The I/O 230 may input and/or output signals, data, information, etc. In some embodiments, the I/O 230 may enable a user interaction with the processing engine 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing engine 140 and the scanner 110, the terminal 130, and/or the storage 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 2-B is a schematic diagram illustrating exemplary hardware and/or software components of an exemplary mobile device on which the terminal may be implemented according to some embodiments of the present disclosure. As illustrated in FIG. 2-B, the mobile device 250 may include a communication platform 260, a display 270, a graphic processing unit (GPU) 271, a processor 272, an I/O 273, a memory 280, and a storage 275. In some embodiments, any other suitable component, including but not limited to a system bus or a controller (not shown), may also be included in the mobile device 250. In some embodiments, a mobile operating system 281 (e.g., iOS™, Android™, Windows Phone™) and one or more applications 282 may be loaded into the memory 280 from the storage 275 in order to be executed by the processor 272. The applications 282 may include a browser or any other suitable mobile apps for receiving and rendering information relating to the determination of the focal point or the displacement of the focal point of the radiation source 115 of the CT scanner 110 from the processing engine 140. User interactions with the information stream may be achieved via the I/O 273 and provided to the processing engine 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 3:
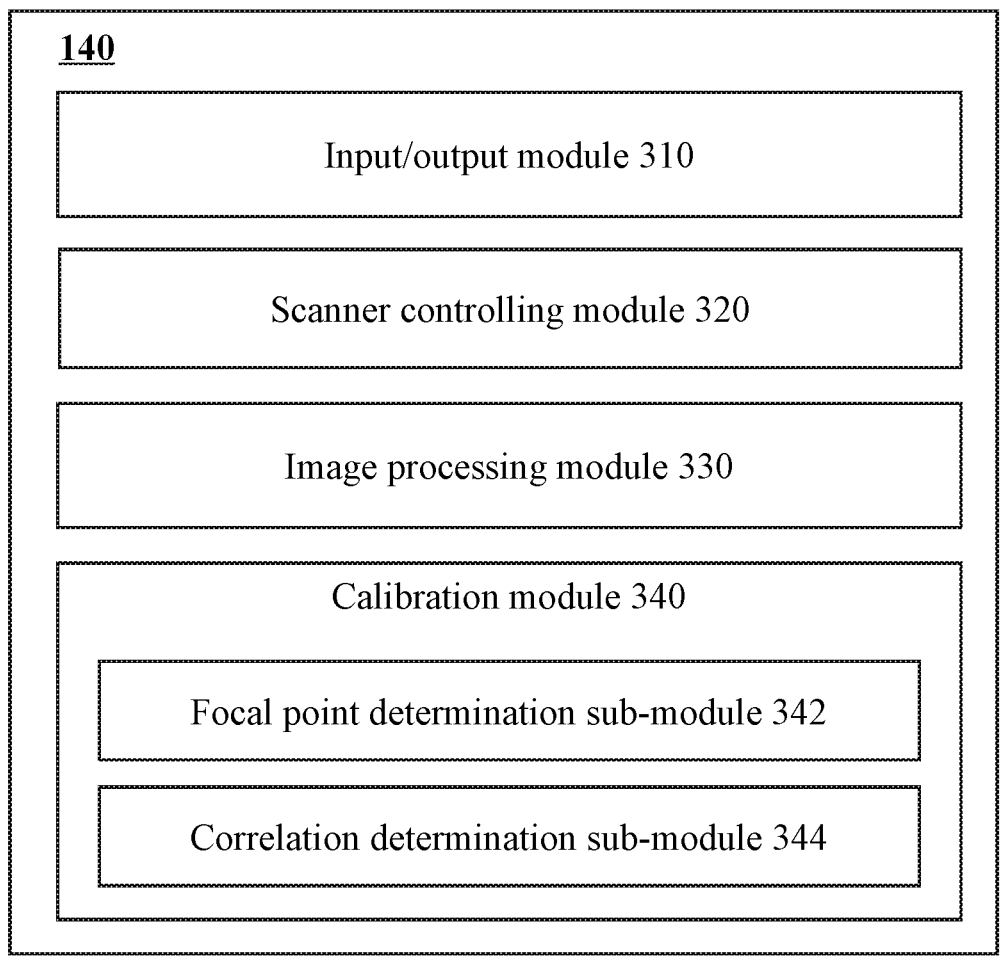

FIG. 3 is a schematic diagram illustrating an exemplary processing engine according to some embodiments of the present disclosure. The processing engine 140 may include an input/output module 310, a scanner controlling module 320, an image processing module 330, and a calibration module 340. Other modules may also be included in the processing engine 140.

The input/output module 310 may be configured to communicate (e.g., acquire, receive, send) data for the processing engine 140. The data may include data generated by the scanner 110, temporary data generated by processing engine 140, control signal generated by the processing engine 140 for controlling the scanner 110, instructions for operating processing engine 140 and/or its modules/units, etc. The data may be communicated with the CT scanner 110, the terminal 130, the network 120, etc.

The scanner controlling module 320 may be configured to generate control signal for controlling the CT scanner 110. The control signal may be generated based on one or more scanning parameters. The scanning parameters may correspond to the type, scanning times, starting time, scanning speed, the scanning region, the scanning condition, etc., of the scanning to be performed or being performed by the scanner 110. The generated control signal may be sent to the CT scanner 110 to control or guide the CT scanner 110 for performing a scanning on a subject.

One or more of the scanning parameters may be provided by a user through the terminal 130, be acquired from a resource via the network 120, be acquired from a storage device (e.g., the storage 150, the storage 220, the memory 280), or the like, or a combination thereof. One or more of the scanning parameters may also be determined by one or more modules/units of processing engine 140 (e.g., calibration module 340).

The image processing module 330 may be configured to generate (or reconstruct) an image based on the scan date acquired by the scanner 110. Different image reconstruction techniques or data processing techniques may be adopted by the image processing module 330.

In some embodiments, the image processing module 330 may reconstruct one or more slice images based on the acquired date. A slice image may be a 2D cross-sectional image of the scanned subject. The obtained one or more slice images may be directly used for viewing the inside of the scanned subject. Alternatively or additionally, a plurality of slice images may be used for generating a volume image for enhancing the visual experience. In some embodiments, image processing module 330 may directly reconstruct a volume image without generating a plurality of slice images first during the reconstruction process.

The calibration module 340 may be configured to assess the performance of one or more devices, modules and/or units of the CT system 100 and obtain one or more performance parameters. For example, the one or more performance parameters may relate to the imaging performance of the CT scanner 110. The calibration module 340 may be further configured to adjust (or calibrate) the settings of the one or more devices, modules and/or units (e.g., the CT scanner 110) of the CT system 100 based on the obtained performance parameters.

The calibration module 340 may include a focal point determination sub-module 342. The focal point of the CT scanner 110 may be displaced (e.g., moved, vibrated, oscillated) during its usage (detailed description are provided in connection with FIG. 4-A). The focal point determination sub-module 342 may be configured to determine the displaced focal point of the radiation source 115. In some embodiments, the focal point determination sub-module 342 may determine the displacement of the focal point of the radiation source using a non-uniform ASG (type I and/or type II) according to process 500 described in connection with FIG. 5. The displaced focal point (second focal point) may be expressed in terms of a coordinate or a displacement along the X direction and or the Z direction relative to the original (or intended) focal point (first focal point). In the present disclosure, unless otherwise noted, "displacement" is a vector which includes both the displacement value and the displacement direction.

In some embodiments, during the process 500, a parameter (e.g., a ratio of a first radiation intensity to a second radiation intensity of two director units) may be obtained as an intermediate for determining the displaced focal point. The calibration module 340 may further include a correlation determination sub-module 344. The correlation determination sub-module 344 may be configured to determine the correlation (e.g., in the form of a lookup table, a function) between the parameter obtained in process 500 and the focal point. The correlation may then be used to determine the displaced focal point in process 500.

It may be noted that, the above description about processing engine 140 is only for illustration purposes, and is not intended to limit the present disclosure. It is understandable that, after learning the major concept and the mechanism of the present disclosure, a person of ordinary skill in the art may alter processing engine 140 in an uncreative manner. The alteration may include combining and/or splitting modules or sub-modules, adding or removing optional modules or sub-modules, etc. All such modifications are within the protection scope of the present disclosure.

FIG. 4-A is a schematic diagram illustrating the effect of the change of the focal point of the radiation source in the CT scanner. For demonstration purposes, the effect of the change of the focal point is described with a standard ASG (e.g., ASG 410). In the present disclosure, the plates (e.g., plates 410-1~410-5) of a standard ASG may have the same or substantially the same shape, size (including length, width, and height), and made of the same material(s). The cells defined by the plates of the standard ASG may also have the same or substantially the same shape and/or size. Cells (e.g., cell 411) of the standard ASG may each include only one detector unit (e.g., detector units 412-1~412-4). The plates of the standard ASG 410 are aligned toward a first focal point (the original or intended focal point, e.g., focal point 415) of the radiation source 115. Standard ASGs have been widely adopted in the prior art.

During the usage of the CT scanner 110, the focal point of the radiation source 115 may be displaced (e.g., moved, vibrated, oscillated) due to various factors. The various factors may include, for example, the thermal expansion and/or contraction of the radiation source 115 during the emitting of radiation beams, the gravity, the centrifugal force, the vibration of the radiation source 115 caused by the running of CT scanner 110, the aging of the mechanical structure(s) of CT scanner 110, the imaging technique adopted by the CT scanner 110 (e.g., z-flying focal spot technology), or the like, or a combination thereof. A deviation of the focal point of the radiation source 115 from its intended position may be expressed in terms of one or more deviation component(s) along the X, Y and/or Z direction. In some embodiments, the deviation component along the Y direction may show a negligible influence and may be omitted.

At a certain time point, the radiation source 155 may have a second focal point (e.g., focal point 416). As the plates of ASG 410 are aligned toward the focal point 415, some primary radiation beams (e.g., radiation beam 419) may still find their way passing through the ASG 410 to the detector units (e.g., detector units 412-2), while some of the primary radiation beams (e.g., radiation beam 418) may be blocked by the plates (e.g., plate 410-2) of the ASG 410. As a result, a part (e.g., part 413-1) of each of at least some detector units may receive fewer radiation beams compared to the other part (e.g., part 413-2), and a shadow may form (e.g., shadow 414-1~414-4). The existence of shadows may cause a reduction of the intensity of radiation received by a detector unit, which may in turn result in a reduction of the quality of an image generated therefrom (e.g., in the form of artifacts or reduced resolution).

When the standard ASG 410 is used, after the change or displacement of the focal point, the reductions of the radiation intensities occurred on all the detector units may be to the same or similar degree.

The reduction of the image quality caused by shadows may be compensated (e.g., by the calibration module 340 and/or the Image processing module 330) using various hardware related (e.g., focus point tracing) or software related (e.g., image post-processing) techniques. These techniques may involve the determination of the displaced focal point (e.g., the location of a displace focal point (or referred to as a second focal point) relative to the original or intended focal point (or referred to as the first focal point)). Theoretically, the second focal point may be determined based on the reduction of the radiation intensity detected by one (or more for eliminating errors) of the detector units. However, besides the change of the focal point, one or more other factors (e.g., mA modulation, kV ripple, mA ripple, filament establishment) may also cause the reduction of the radiation intensity upon all the detector units. With a standard ASG, it is difficult to differentiate the portion of the reduction of the radiation intensity caused by the displacement of the focal point from the portion of the reduction caused by the one or more other factors.

In the present disclosure, the CT scanner 110 may be equipped with a non-uniform ASG for identifying the reduction of the radiation intensity caused by the displacement of the focal point. In some embodiments, the focal point determination sub-module 342 may determine the displaced focal point using the non-uniform ASG according to process 500 descripted in connection with FIG. 5. The non-uniformity may be effectuated by the arrangements of the plates of an ASG, the sizes of the plates, the materials of the plates, or the like, or a combination thereof. For instance, in a non-uniform ASG, cells formed by the plates enclose different numbers of detector units. As another example, a non-uniform ASG may be formed by plates of different shapes or sizes (e.g., different heights). FIGS. 4-B, 4-C, and 4-D illustrate exemplary non-uniform ASGs according to some embodiments of the present disclosure. It may be noted that, FIGS. 4-B, 4-C, and 4-D are only provided for demonstration purposes and not intend to limit the scope of the present disclosure. The illustrated non-uniform ASGs are nonexclusive and may have different forms when applied in practical use.

FIG. 4-B illustrates an exemplary non-uniform ASG according to some embodiments of the present disclosure. ASG 420 may be installed as a type II non-uniform ASG. ASG 420 may be equipped on the CT scanner 110 for facilitating the determination of a displaced or second focal point 426 relative to an intended or first focal point 425 according to, for example, process 500 described in connection with FIG. 5. The plates (e.g., plates 420-1~420-3) of the ASG 420 may also have the same or substantially the same shape, size, and be made of the same material(s). The cells defined by the plates of the ASG 420 may also have the same or substantially the same configuration (e.g., shape and size). Distinguished from a standard ASG (e.g., ASG 410), a cell (e.g., cell 421) of ASG 420 may include more than one detector units (e.g., detector units 422-1~422-4) along at least one direction (e.g., X direction, Z direction, or both). For instance, each cell of ASG 420 may include two detector units (four in total) along both the X direction and the Z direction.

The plates of ASG 420 may be aligned toward the first focal point 425 (the original or intended focal point) of the radiation source 115. When the focal point of the radiation source 115 changes from the first focal point 425 to the second focal point 426, some detector units (first detector units, e.g., detector units 422-1-And 422-3) may be covered by the shadows (e.g., shadows 424-1 and 424-2) caused by the displacement of the focal point, while some detector units (second detector units, e.g., detector unit 422-2 and 422-4) may be free of the shadows caused by the same reason. As used herein, a first detector unit may refer to a detector unit that receives or detects a different amount of radiation when the focal point of the radiation source is displaced compared to when the focal point of the radiation source is at its original or intended location, assuming that the radiation source emits the same amount of radiation beams regardless of the location of its focal point. As used herein, a second detector unit may refer to a detector unit that receives the same (or substantially the same) amount radiation when the focal point of the radiation source is displaced from its original or intended location, assuming that the radiation source emits the same amount of radiation beams regardless of the location of its focal point. The reductions of the radiation intensities caused by the change of the focal point detected by the first detector units may be different from the one detected by the second detector units. The difference may be used (e.g., by the focal point determination sub-module 342) for determining the second focal point 426.

It may be noted that, the first detector units and the second detector units may exchange their roles as a first detector unit at least partially covered by shadow or a second detector unit free of shadow when the focal point is displaced along the direction opposite to that illustrated in FIG. 4-B. For example, the second detector units 422-2 and 422-4 may be covered by shadows caused by the displacement of the focal point, while the first detector units 422-1 and 422-3 may be free of shadows caused by the same reason. However, the difference between the radiation intensities of the first detector units and the second detector units may still be used for determining the second focal point 426.

The radiation intensities of a first-second detector unit pair (e.g., the detector units 422-1 and 422-2, the detector units 422-2 and 422-3, or the detector units 422-1 and 422-4) may be used for determining the second focal point 426. In some embodiments, the radiation intensities of at least one arbitrary or predetermined pair of adjacent first detector unit and second detector unit (e.g., the detector units 422-2 and 422-3) may be used for determining the second focal point 426.

FIG. 4-C illustrates an exemplary non-uniform ASG according to some embodiments of the present disclosure. ASG 430 may be equipped on the CT scanner 110 for facilitating the determination of a displaced or second focal point 436 relative to an intended or first focal point 435 according to, for example, process 500 described in connection with FIG. 5. The plates (e.g., plates 440-1~440-5) of the ASG 430 may still have same or substantially same shapes, sizes, and the materials. The cells of ASG 430, however, may not be uniformly configured. One or more cells (the irregular cells, e.g., cell 431-1) of ASG 430 may include more than one detector units (e.g., detector units 432-1 and 432-2 as illustrated in FIG. 4-C) along at least one direction (e.g., the X direction, the Z direction, or both). For instance, ASG 430 may have one or more irregular cells including two detector units (two in total) along X direction and one or more irregular cells including two detector units (two in total) along Z direction. As another example, ASG 430 may have one or more irregular cells including two detector units (four in total) along both the X direction and the Z direction. The plates of ASG 430 may be aligned toward the first focal point 435 (the original or intended focal point) of the radiation source 115. As used herein, a regular cell may refer to one that encloses one detector unit (e.g., cells 431-2 and 431-3 as illustrated in FIG. 4-C). As used herein, an irregular cell may refer to one that encloses more than one detector unit (e.g., the cell 431-1 as illustrated in FIG. 4-C).

In the ASG 430, only a detector unit (e.g., detector units 432-1 and 432-2) enclosed within an irregular cell may be designated as a first detector unit that is at least partially covered by the shadow or a second detector unit that is free of the shadow occurred when the focal point of the radiation source is displaced. Other detector units (e.g., detector units 432-3 and 432-4) enclosed in regular cells may always be covered by shadows (e.g., shadows 434-2 and 434-3) when the focal point is displaced regardless of the direction of the displacement, and are not included in determining the focal point.

When the focal point of the radiation source 115 is displaced from the first focal point 435 to the second focal point 436, a first detector unit (e.g., the detector unit 432-1) within an irregular cell may be covered by the shadow (e.g., shadow 434-1) caused by displacement of the focal point, while a second detector unit (e.g., detector unit 432-2) within a same irregular cell or different irregular cells may be free of the shadows caused by the same reason. The difference between the radiation intensities received by the first detector unit and the second detector unit may be used (e.g., by the focal point determination sub-module 342) for determining the second focal point 436. It may also be noted that, the first detector unit(s) and the second detector unit(s) may exchange their roles when the focal point is displaced along the along the direction opposite to that illustrated in FIG. 4-C.

In some embodiments, the radiation intensities of a first detector unit and a second detector unit within an arbitrary or predetermined irregular cell may be used (e.g., by focal point determination sub-module 342) for determining the second focal point 436. The first detector unit and the second detector unit may be adjacent to one another.

FIG. 4-D illustrates an exemplary non-uniform ASG according to some embodiments of the present disclosure. ASG 440 may be equipped on the CT scanner 110 for facilitating the determination of a displaced or second focal point 446 relative to an intended or first focal point 445 according to, for example, process 500 described in connection with FIG. 5. One or more plates (the abnormal plates, e.g., plates 440-2) may have different shapes and/or sizes compared to other plates (e.g., plates 440-1, 440-2, 440-3 and 430-4) of the ASG 440. Each cell of the ASG 440 may enclose one detector unit (e.g., detector units 442-1~442-4). A cell (e.g., cells 441-1 and 441-2 as illustrated in FIG. 4-D) surrounded by one or more (along either or both of the X direction and the Z direction) abnormal plates may be referred to as an abnormal cell. One abnormal plate may define a pair of abnormal cells. For instance, the ASG 440 may include one or more pairs of abnormal cells with one or more abnormal plates along either or both of the X direction and the Z direction. The plates of ASG 430 may be aligned toward the first focal point 435 (the original or intended focal point) of the radiation source 115. As used herein, a regular cell may refer to one that encloses one detector unit (e.g., the cell enclosing detector unit 432-3 and the cell enclosing 432-4 as illustrated in FIG. 4-D.). As used herein, normal plates may refer to the majority of plates included in an ASG which may share a same size (e.g., height). An abnormal plate may refer to one that has a different size compared to the normal plates (e.g., the plate 440-2 as illustrated in FIG. 4-D). An abnormal cell may refer to one that surrounded by one or more abnormal plates (e.g., the cells 441-1 and 441-2 as illustrated in FIG. 4-D).

In the ASG 440, only a detector unit (e.g., detector units 442-1 and 442-2) enclosed within an abnormal cell may be designated as a first detector unit that is at least partially covered by the shadow or a second detector unit that is free of the shadow occurred when the focal point of the radiation source is displaced. Other detector units (e.g., detector units 442-3 and 442-4) may always be covered by shadows (e.g., shadows 444-2 and 444-3) when the focal point is displaced regardless of the direction of the displacement, and are not included in determining the focal point.

When the focal point of the radiation source 115 is displaced from the first focal point 445 to the second focal point 446, a first detector unit (e.g., the detector unit 444-1) within an abnormal cell may have a larger part covered by the shadow (e.g., shadow 444-1) caused by the displacement of the focal point, while a second detector unit (e.g., detector unit 442-2) within another abnormal cell (e.g., an adjacent one which shares a same abnormal plate) may have a smaller part covered by the shadow caused by the same reason. The difference between the radiation intensities received by the first detector unit and the second detector unit may be used (e.g., by the focal point determination sub-module 342) for determining the second focal point 446. It may also be noted that, the first detector unit(s) and the second detector unit(s) may exchange their roles when the focal point is displaced along the direction opposite to that illustrated in FIG. 4-D.

In some embodiments, the radiation intensities of a first detector unit and a second detector unit within an arbitrary or predetermined pair of abnormal cells may be used (e.g., by focal point determination sub-module 342) for determining the second focal point 446. The first detector unit and the second detector unit may be adjacent to one another.

It may be noted that, the non-uniform ASG illustrated in FIG. 4-B, FIG. 4-C, and FIG. 4-D are provided only for demonstration purposes, and are not intended to be limiting. Numerous modification may be made to the ASG 410, 420, or 430. For example, the cells of ASG 410, the irregular cell(s) of ASG 420, or the abnormal cell(s) of ASG 430 may include more detector units along either or both of the X direction and the Z direction.

In some embodiments, ASG 410 may also be made as a non-uniform ASG by using different material with different radiation blocking (or absorbing) properties for different plates. For example, one or more of the plates of ASG 410 (e.g., the plate 410-2) may have smaller radiation blocking capacities compared to other plates. When the focal point of radiation 115 is displaced from the first focal point 415 to the second focal point 416. The shadow region of detector 412-2 may receive more radiation than other shadow regions. When the focal point of radiation 115 is displaced along the direction opposite to that illustrated in FIG. 4-A, the shadow region of detector 412-1 may receive more radiation than other shadow regions. The detector unit 412-1 may be assigned as the first detector unit receiving reduced radiation, and the detector unit 412-2 may be assigned as the second detector unit receiving the same amount of radiation when the focal point is displaced compared to when the focal point is located at its original or intended position.

Figure 5:
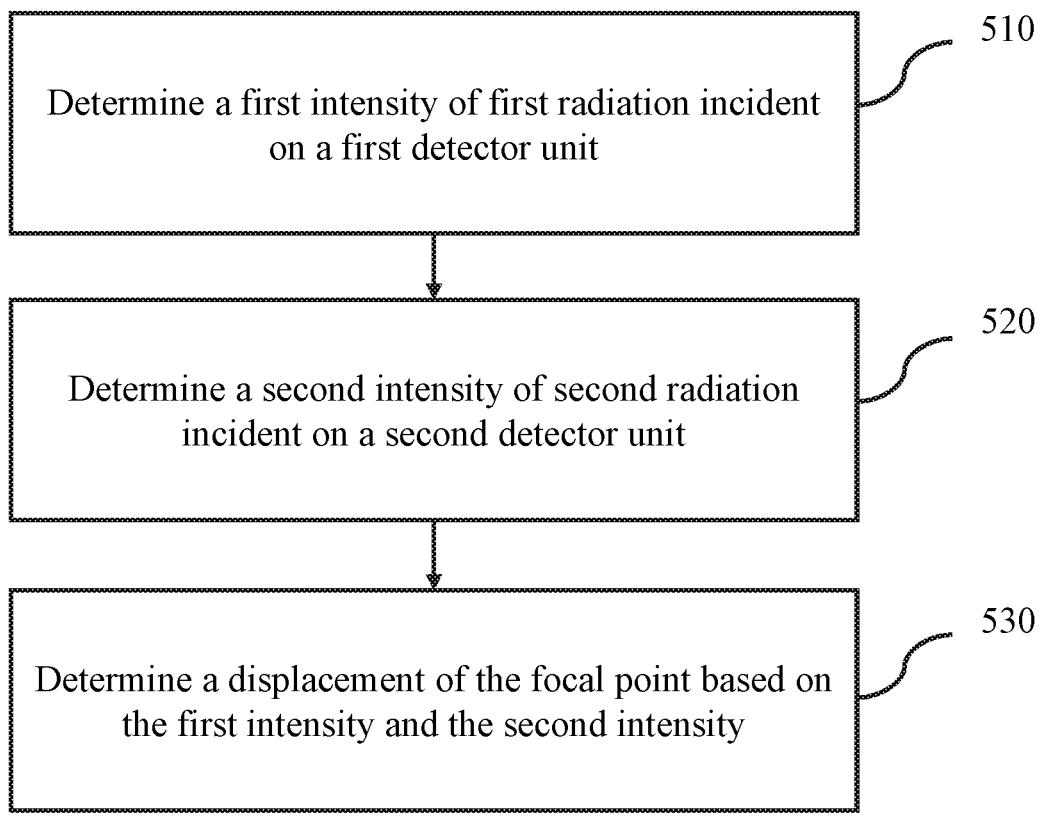
FIG. 5 is a schematic diagram illustrating an exemplary process for determining the focal point of the radiation source according to some embodiments of the present disclosure.

FIG. 5 is a schematic diagram illustrating an exemplary process for determining the focal point of the radiation source according to some embodiments of the present disclosure. Process 500 may be performed by the focal point determination sub-module 342 for determining the focal point of a radiation source belonging to a CT scanner 110 equipped with one or more non-uniform ASG (type I and/or type II). The CT scanner 110 may include only the non-uniform ASG, or include both the standard ASG and the non-uniform ASG. In some embodiments, one or more operations of process 500 illustrated in FIG. 5 for determining the focal point of the radiation source may be implemented in the CT system 100 illustrated in FIG. 1. For example, the process 500 illustrated in FIG. 5 may be stored in the storage 150 in the form of instructions, and invoked and/or executed by the processing engine 140 (e.g., the processor 210 of the computing device 200 as illustrated in FIG. 2-A).

The focal point determination sub-module 342 may determine a displacement of the focal point from a first focal point to a second focal point via process 500 along the X direction or the Z direction. The displacement may then be used to generate the coordinate of the second focal point, or be directly used (e.g., by the calibration module 340 and/or the Image processing module 330) for compensating the reduction of the image quality caused by the change of focal point via one or more hardware related (e.g., focus point tracing) and/or software (e.g., image post-processing) related techniques. In some embodiments, a calibration instruction for calibrating the CT scanner 110 may be generated by the calibration module 340 and/or the scanner controlling module 320 and sent to the CT scanner for calibration.

In 510, the focal point determination sub-module 342 may determine a first intensity of first radiation incident on a first detector unit of the CT scanner 110. In 520, the focal point determination sub-module 342 may determine a second intensity of second radiation incident on a second detector unit of the CT scanner 110. The first radiation and the second radiation may be emitted from the radiation source 115 with the second focal point. The first radiation and the second radiation may be emitted at a same time point or within a same time interval.

The CT scanner 110 may include a non-uniform ASG as described in connection with FIGS. 4-B to 4-D. The first detector unit and the second detector unit may be determined by a user, by the focal point determination sub-module 342, or the like, or a combination thereof. The first detector unit and the second detector unit may be determined based on the structure of the non-uniform ASG (see the descriptions of FIGS. 4-B to 4-D). In some embodiments, the first detector unit and the second detector unit adjacent to one another may be determined. In some embodiments, the first detector unit and the second detector unit spaced apart may be determined.

In some embodiments, the ASG 420 may be the non-uniform ASG installed on the CT scanner 110. The first detector unit and the second detector unit may be included in the same cell. For example, the detector units 422-1 and 422-2 may be determined as the first detector unit and the second detector units. Alternatively or additionally, the first detector unit and the second detector unit may be included in different cells. The different cells may be adjacent to one another or spaced apart. For example, the detector units 422-2 and 422-3 (or the detector units 422-1 and 422-4) may be determined as the first detector unit and the second detector units.

In some embodiments, the ASG 430 may be the non-uniform ASG installed on the CT scanner 110. The first detector unit and the second detector unit may be included in the same cell. For example, the detector units 432-1 and 432-2 may be determined as the first detector unit and the second detector units. Alternatively or additionally, the first detector unit and the second detector unit may be included in different cells sharing a same (or substantially same) structure. The different cells may be adjacent to one another or spaced apart.

In some embodiments, the ASG 440 may be the non-uniform ASG installed on the CT scanner 110. The non-uniform ASG 440 may include abnormal cells (e.g., cells 441-1 and 441-2). The abnormal cells may include plates of different heights. The first detector unit and the second detector unit may be included in different abnormal cells having different structures. The different abnormal cells may be adjacent to one another or be spaced apart. For example, the detector units 442-1 and 442-2 may be determined as the first detector unit and the second detector unit.

The focal point determination sub-module 342 may determine the first intensity and the second intensity based on the signals generated by the first detector unit and the second detector unit in response to the first radiation and the second radiation, respectively. For example, the first intensity and the second intensity may correspond to the amplitudes, average amplitudes, or integrals of the amplitudes of the corresponding signals over a predetermined time interval. Due to the configuration of the non-uniform ASG, after the displacement of the focal point, the first intensity and the second intensity may become different.

The focal point determination sub-module 342 may determine the first intensity and the second intensity in real time, or based on the scan data (including the information relating to the signals generated by the first detector unit and the second detector unit) stored in a storage device (e.g., storage 150, storage 220, storage 275, memory 280) at a later time. Due to the equivalence of 510 and 520, the two operations may be performed in any sequence or be performed simultaneously.

In 530, the focal point determination sub-module 342 may determine the displacement of the focal point based on the first intensity and the second intensity. The direction (e.g., the X direction, the Z direction) along which the first detector unit and the second detector unit are located may define the direction of the displacement determined. For example, to determine the displacement of the focal point along both the X direction and the Z direction, a first pair of a first detector unit and a second detector unit located along the X direction and a second pair of a first detector unit and a second detector unit located along the Z direction may be selected. Process 500 may then be performed twice for obtaining the displacements along both directions.

In some embodiment, the focal point determination sub-module 342 may determine the displacement of the focal point based at least in part on at least one parameter relating to the configuration of the ASG. For instance, the at least one parameter may include a height of at least some plates of the ASG and a distance from the second focal point to a top of the at least a portion of the ASG. An exemplary process are described in connection with FIGS. 6, 7-A, and 7-B.

Merely by way of example, the focal point determination sub-module 342 may determine the displacement of the focal point based on a ratio of the first intensity detected by the first detection unit to the second intensity detected by the second detection unit. In some embodiments, the focal point determination sub-module 342 may obtain a correlation between the displacement and the ratio, then determine the displacement based on the ratio and the correlation. An exemplary process are described in connection with FIGS. 8 and 9.

In some embodiments, a plurality of pairs of first and second detector units may be used for determining the displacement of the focal point along one direction. The focal point determination sub-module 342 may perform process 500 upon each of the plurality of detector unit pairs to generate a plurality of results, and determine the displacement along that direction based on the plurality of results. Alternatively, the focal point determination sub-module 342 may determine the first radiation intensity and second radiation intensity based on (e.g., mean, integral) the signals generated by the first detector units and the second detector units, respectively.

Process 500 may be performed prior to or during the scanning of a subject using CT scanner 100. The subject may be a phantom, or a test object (e.g., patient). Signals detected by the detector units (e.g., the first detector unit and the second detector unit) used for determining the focal point may be included in, or excluded from, the data used for generating an image of the subject.

It may be noted that the above descriptions of the determining of the focal point are only for demonstration purposes, and not intended to limit the scope of the present disclosure. It is understandable that, after learning the major concept and the mechanism of the present disclosure, a person of ordinary skill in the art may alter process 500 in an uncreative manner. For example, the operations above may be implemented in an order different from that illustrated in FIG. 5. One or more optional operations may be added to the flowcharts. One or more operations may be divided or be combined. All such modifications are within the protection scope of the present disclosure.

FIG. 6 is a schematic diagram illustrating an exemplary process for determining the displacement of the focal point based on the first intensity and the second intensity according to some embodiments of the present disclosure. Process 600 may be performed to achieve 530 of process 500. In some embodiments, process 600 may be performed by the focal point determination sub-module 342. In some embodiments, one or more operations of process 600 illustrated in FIG. 6 for determining the focal point of the radiation source may be implemented in the CT system 100 illustrated in FIG. 1. For example, the process 600 illustrated in FIG. 6 may be stored in the storage 150 in the form of instructions, and invoked and/or executed by the processing engine 140 (e.g., the processor 210 of the computing device 200 as illustrated in FIG. 2).

In 610, the focal point determination sub-module 342 may obtain a reference radiation intensity for at least one of the first detector unit and the second detector unit. The reference radiation intensity may correspond to the intensity of the radiation received by the first detector unit or the second detector when the focal point of the radiation source 115 is at (approximately or precisely) the first focal point. As used herein, "approximately" may indicate that the deviation from the first focal point (the original or intended focal point) is lower than a threshold. In some embodiments, the threshold may be, e.g., 1 micron, 2 microns, 5 microns, 10 microns, 20 microns, 50 microns, 100 microns, etc. In some embodiments, the threshold may be, 1%, 2%, 3%, 4%, 5%, 6%, 8%, 10%, etc., of the range within which the radiation source is allowed to move. The reference radiation intensity may be determined prior to or during the scanning of a subject using CT scanner 100. For example, the reference radiation intensity may be retrieved from a storage device (e.g., storage 150, storage 220, storage 275, memory 280), determined based on one of the system parameters provided with the CT scanner 100. As another example, the reference radiation intensity may be obtained based on one or more signals generated by one or more detector units of the CT scanner 100.

In some embodiments, the reference radiation intensity may be obtained by the following process. The scanner control module 320 may send a control signal to the CT scanner 110. The CT scanner 110 may respond to the control signal, and cause the radiation source 115 to emit radiation. During the radiation emission process, the temperature of the radiation source 115 may rise (e.g., by running the radiation source 115 originally at a sleep mode or a low-load mode), or drop (e.g., by cooling the radiation source 115 originally at an operative mode or a high-load mode). The focal point of the radiation source 115 may be displaced due to thermal expansion or contraction accordingly.

The signals generated by the first detector unit and the second detector unit may be extensively collected (e.g., 1~500 samples per second) during the radiation emission process. A plurality of first intensities and second intensities may be obtained. When the sum of the first intensity and the second intensity collected at a time point (time point A) reaches its maximum compared to other time points, the focal point of the radiation source 115 at the time point A may be considered as the one (the first focal point) toward which the plates of the ASG are aligned. In some embodiments, the first intensity and the second intensity collected at the time point A may be selected (e.g., by a user or by the focal point determination sub-module 342) as reference radiation intensities for the first detector unit and the second detector unit, respectively. In some embodiments, the average value (weighted or not weighted) of the first intensity and the second intensity of the time point A may be determined (e.g., by a user or by the focal point determination sub-module 342) as one reference radiation intensity for both the first detector unit and the second detector unit.

In some embodiments, a plurality of pairs of first and second detector units may be used for determining the displacement of the focal point along one direction. The focal point determination sub-module 342 may obtain one or more reference radiation intensities for each of the plurality of detector unit pairs. Alternatively, the focal point determination sub-module 342 may determine a common reference radiation intensity set (including one or more reference radiation intensities) for the plurality of detector unit pairs.

The obtained one or more reference radiation intensities may then be stored in a storage device (e.g., storage 150, storage 220, storage 275, memory 280) When the focal point determination sub-module 342 is to determine the displacement of the focal point through process 600, the focal point determination sub-module 342 may obtain at least one of the reference radiation intensities.

In 620, the focal point determination sub-module 342 may obtain at least one ASG parameter relating to the configuration of the non-uniform ASG. The ASG parameter may relate to the height of at least a portion of the ASG, the distance form the second focal point to a top of the at least a portion of the ASG, the length and/or the width of one or more cells of the ASG, or the like, or a combination (e.g., a calculation) thereof. The ASG parameter may be retrieved from a storage device (e.g., storage 150, storage 220, storage 275, memory 280), determined based on one of the system parameters provided with the non-uniform ASG, or measured by a user of the ASG or the CT scanner 110, or a combination thereof.

In 630, the focal point determination sub-module 342 may determine the displacement of the focal point based on the at least one reference radiation intensity obtained in 610, the at least one ASG parameters obtained in 620, the first intensity obtained in 510, and the second intensity obtained 520. The direction (e.g., the X direction, the Z direction) along which the first detector unit and the second detector unit are located may define the direction of the displacement determined in 630.

In some embodiments, the focal point determination sub-module 342 may perform the process 600 according to the description of FIGS. 7-A and 7-B.

FIGS. 7-A and 7-B are schematic diagrams of the process illustrated in FIG. 6 according to some embodiments of the present disclosure. It may be noted that, for demonstration purposes, FIGS. 7-A and 7-B only illustrate the process 600 with the non-uniform ASG 420 as illustrated in FIG. 4-B. However, other non-uniform ASGs (e.g., ASGs 430 and 440 illustrated in FIGS. 4-C and 4-D) described or implied in the present disclosure may also be used for the process 600 with a similar manner.

The plates (e.g., the plates 420-1, 420-2, and 420-3) of the ASG 420 are aligned toward a focal point 710 (first focal point). During the operation of the CT scanner 110, the focal point of the radiation source 115 may be displaced along the X direction or the Z direction (parallel to the detector units). For example, the focal point may be displaced toward one direction to the focal point 712 (as shown in FIG. 7-A), or toward the opposite direction to the focal point 714 (as shown in FIG. 7-B). The focal point being at focal point 712 may cause shadows 724-1 and 724-2 on the first director units 422-1 and 422-3. The focal point being at focal point 714 may cause shadows 724-3 and 724-4 on the first director units 422-2 and 422-4.

For the ASG 420, any pair of adjacent detector units including a first detector unit and a second detector unit may be identified (e.g., by a user or by the focal point determination sub-module 342). In FIGS. 7-A and 7-B, detector unit 422-2 and 422-3 are determined as the first detector unit and the second detector unit, respectively.

The focal point determination sub-module 342 may determine the direction of the displacement by comparing the changes of the radiation intensities occurred on the detector units 422-2 and 422-3. For example, when the detector unit 422-3 has a larger reduction of the radiation intensity (e.g., caused by shadow 724-2), the focal point determination sub-module 342 may determine that the displacement has occurred in a pattern as shown in FIG. 7-A. When the detector unit 422-2 has a larger reduction of the radiation intensity, the focal point determination sub-module 342 may determine the displacement has occurred in a pattern as shown in FIG. 7-B.

In some embodiments, the focal point determination sub-module 342 may directly compare the radiation intensities of the detector units 422-2 and 422-3 for determining the direction of the displacement. The one with a smaller intensity may be determined as the one having a larger reduction of the radiation intensity.

In some embodiments, the focal point determination sub-module 342 may first determine the reductions of the radiation intensities occurred on each of the detector units 422-2 and 422-3 with the corresponding reference radiation intensities obtained in 610. For example, the focal point determination sub-module 342 may obtain a ratio of the currently received radiation intensity to the corresponding reference radiation intensity for each of the detector units 422-2 and 422-3. The one with a smaller ratio may be determined as the one having a larger reduction of the radiation intensity.

In some embodiments, when the displacement is determined to have occurred in a pattern as shown in FIG. 7-A, the focal point determination sub-module 342 may determine the displacement according to Equation (1) in 630 of process 600, which may be expressed as:

$$D_1 = \left(1 - \frac{I_2}{I_{R2}}\right)\frac{L_2 H_{F2A}}{H_{ASG}}, \tag{1}$$

where $D_1$ is the value of the displacement in a pattern as shown in FIG. 7-A, $I_2$ is the intensity (second intensity) of the radiation received by the detector unit 422-3 (second detector unit), $I_{R2}$ is the reference radiation intensity for the detector unit 422-3, $L_2$ is the length of the detector unit 422-3 in the X direction or the Z direction, $H_{ASG}$ is the height of the plate (e.g., plate 420-2) of the ASG 420 shared by the detector units 422-2 and 422-3, and $H_{F2A}$ is the distance from the second focal point to the top of the shared plate in a direction perpendicular to the detector 422-2 and/or 422-3 (e.g., the Y direction). As the displacement along the Y direction is omitted, $H_{F2A}$ may be considered as the distance from the first focal point to the top of the shared plate in the Y direction.

In some embodiments, when the displacement is determined to have occurred in a pattern as shown in FIG. 7-B, the focal point determination sub-module 342 may determine the displacement according to Equation (2) in 630 of process 600, which may be expressed as:

$$D_2 = \left(1 - \frac{I_1}{I_{R1}}\right)\frac{L_1 H_{F2A}}{H_{ASG}}, \tag{2}$$

where $D_2$ is the value of the displacement in a pattern as shown in FIG. 7-B, $I_1$ is the intensity (first intensity) of the radiation received by the detector unit 422-2 (first detector unit), $I_{R1}$ is the reference radiation intensity for the detector unit 422-2, $L_1$ is the length of the detector unit 422-2 in the X direction or the Z direction, and $H_{ASG}$ and $H_{F2A}$ hold the same meaning as in Equation (1).

$H_{ASG}$ and $H_{F2A}$ may be obtained as ASG parameters in 620 of process 600. $H_{ASG}$ and $H_{F2A}$ may be provided with CT scanner 110 or ASG 420 as system parameters, or be measured directly by a user.

$L_1$ and $L_2$ may have a same value or different values. In some embodiments, $L_1$ and $L_2$ may be provided with CT scanner 110 as system parameters or be measure form the CT scanner 110 by a user. In some embodiments, $L_1$ and $L_2$ may be obtained as or determined based on the ASG parameters in 620 of process 600. For example, $L_1$ and $L_2$ may be considered as half of the length of the cells defined by the plates 420-1, 420-2, and 420-3 in the X direction or the Z direction.

In some embodiments, $L_1$ and $L_2$ may both have a same value L. A parameter with a value of $LH_{F2A}/H_{ASG}$ may be provided with CT scanner 110 or ASG 420, and be obtained as part of the ASG parameter in 620 of process 600.

$I_{R1}$ and/or $I_{R2}$ may be obtained in 610 of process 600. In some embodiments, both of $I_{R1}$ and $I_{R2}$ may be obtained in 610. For example, $I_{R1}$ and $I_{R2}$ may be used to determine the pattern of the displacement. In some embodiments, the pattern of the displacement may be determined without using $I_{R1}$ or $I_{R2}$ (e.g., by directly comparing the radiation intensities of the detector units 422-2 and 422-3), and one of $I_{R1}$ or $I_{R2}$ may be obtained in 610 according to the determined pattern. In some embodiments, $I_{R1}$ and/or $I_{R2}$ may be replaced by the radiation intensity of the detector unit free of shadow caused by the displacement of the focal point. For example, to determine $D_1$, $I_1$ may be used to replace $I_{R2}$ in Equation (1); to determine $D_2$, $I_2$ may be used to replace $I_{R1}$ in Equation (2).

FIG. 8 is a schematic diagram illustrating an exemplary process for determining the displacement of the focal point based on the first intensity and the second intensity according to some embodiments of the present disclosure. Process 800 may be performed to achieve 530 of process 500. Process 800 may be performed by the focal point determination sub-module 342. In some embodiments, one or more operations of process 800 illustrated in FIG. 8 for determining the focal point of the radiation source may be implemented in the CT system 100 illustrated in FIG. 1. For example, the process 800 illustrated in FIG. 8 may be stored in the storage 150 in the form of instructions, and invoked and/or executed by the processing engine 140 (e.g., the processor 210 of the computing device 200 as illustrated in FIG. 2).

In 810, the focal point determination sub-module 342 may determine a ratio of the first intensity to the second intensity. Then in 820, the focal point determination sub-module 342 may obtain a correlation between the ratio and the displacement of the focal point. The correlation may be, for example, a mathematical function (e.g., a polynomial, a piecewise function), or a lookup table (the items of which may each include a ratio and a corresponding displacement), etc. In 830, the focal point determination sub-module 342 may determine the displacement of the focal point based on the ratio and the correlation. For example, the displacement may be obtained by inputting the ratio into the mathematical function, or by searching the item with the same (precisely or approximately) ratio in the lookup table. In some embodiments, an interpolation or extrapolation may be performed to determine a displacement based on the values available in the lookup table.

The correlation between the ratio and the displacement of the focal point may be generated by the correlation determination sub-module 344. An exemplary technique for generating the correlation is discussed in connection with FIG. 9.

FIGS. 9-A and 9-B are schematic diagrams illustrating exemplary techniques for generating the correlation between the ratio of the first intensity to the second intensity and the displacement of the focal point according to some embodiments of the present disclosure. Detector 950 may be the same as or similar to the detector 112. Detector 950 may include a plurality of detector units and one or more non-uniform ASGs (not shown in FIG. 9 for simplicity). The one or more non-uniform ASGs may be configured according to a focal point 901 (first focal point) of the radiation source 115. A plate 910 made of radiation absorbing material may be placed between the radiation source 115 and the detector 950 for determining the correlation. The plate 910 may have a pinhole 915 through which a portion of the radiation emitted by the radiation source 115 may pass and reach the detector 950. A line 960 linking the center point of the pinhole 915 and the focal point 901 may coincide with or parallel to (approximately or precisely) the Y direction. When the focal point of the radiation source 115 is at the focal point 901, a region $R_1$ of detector 950 may be illuminated by the radiation emitted from the radiation source 115.

To determine the correlation between the ratio of the first intensity (detected by a first detector unit) to the second intensity (detected by a first detector unit) and the displacement of the focal point of the radiation source, the scanner control module 320 may send a control signal to the CT scanner 110. The CT scanner 110 may respond to the control signal, and cause the radiation source 115 to emit radiation. During the radiation emission, the temperature of the radiation source 115 may rise (e.g., by running the radiation source 115 originally at a sleep mode or a low-load mode), or drop (e.g., by cooling the radiation source 115 originally at an operative mode or a high-load mode). The focal point of the radiation source 115 may be displaced due to thermal expansion or contraction accordingly.

At a time point B, the focal point of the radiation source 115 may be displaced to the focal point 902. A region $R_2$ of the detector 950 may be illuminated by the radiation emitted from the radiation source 115 at the time point B. The focal point 902 is an arbitrary focal point of the radiation source 115 between the focal point 901 and the farthermost focal point the radiation source 115 may ever have along the X direction or the Z direction.

In some embodiments, as illustrated in FIG. 9-A, to determine the displacement from the focal point 901 to the focal point 902, the correlation determination sub-module 344 may determine a distance x between the farther edge (indicated by line 961) of region $R_2$ (relative to the focal point 901) and the intersection point of the surface of the detector 950 and line 960. For example, to determine x, the correlation determination sub-module 344 may locate an illuminated (or not illuminated) detector unit locating at (approximately or precisely) the farther edge of region $R_2$ based on the signals generated by the detector units. The detector unit locating at the farther edge of region $R_2$ may be determined as the ith detector unit. The correlation determination sub-module 344 may also locate the detector unit locating at (approximately or precisely) the intersection point, for example, based on the structure information of the CT scanner 110. For instance, the CT scanner 110 may be configured that the focal point 901 is right above (approximately or precisely) a certain detector unit (e.g., detector unit locating at the center of the detector 950) along the Y direction, and the related structure information may be pre-stored in a storage device (e.g., the storage 150, the storage 220, the storage 275, and memory 280). The detector unit locating at the intersection point may be determined as the jth detector unit. The correlation determination sub-module 344 may obtain x by multiplying the length (or average length) of the detector units with the absolute value of (j−i). Alternatively or additionally, the correlation determination sub-module 344 may obtain x based on i, j (optional), and a look-up table correlating x, i and j (optional).

The correlation determination sub-module 344 may then determine the displacement D from the focal point 901 to the focal point 902 via Equation (3), which may be express as:

$$D = \left(x - \frac{d}{2} * \frac{(H_{F2P} + H_{P2D})}{H_{F2P}}\right) * \frac{H_{F2P}}{H_{P2D}}, \quad (3)$$

where $H_{F2P}$ is the distance between the focal point 902 (or focal point 901 as the displacement along the Y direction is omitted) and the central plane (dashed line) of plate 910 along the Y direction, $H_{P2D}$ is the distance between the central plane of the plate 910 and the detector 950 along the Y direction, and d is the diameter of the pinhole 915. $H_{F2P}$, $H_{P2D}$ and d may be provided with the CT scanner 110 and/or plate 910, or be directly measured by a user.

Alternatively or additionally, the correlation determination sub-module 344 may obtain D based on i, j (optional), and a look-up table correlating D, i and j (optional).

In some embodiments, as illustrated in FIG. 9-B, to determine the displacement from the focal point 901 to the focal point 902, the correlation determination sub-module 344 may determine a distance x' between the centroid of region $R_2$ and the centroid of region $R_1$. For example, to determine x', the correlation determination sub-module 344 may determine the region $R_2$ and region $R_1$ and their relative position (e.g., the position of one of the region $R_2$ and region $R_1$ relative to the position of the other) based on the signals generated by the detector units and the structure information of the detector 950. The correlation determination sub-module 344 may then determine the centroids of region $R_2$ and region $R_1$ and the distance x'. Merely by way of example, the correlation determination sub-module 344 may then determine the displacement D from the focal point 901 to the focal point 902 according to Equation (4), which may be express as:

$$D = x' * \frac{H_{F2P}}{H_{P2D}}, \quad (4)$$

where $H_{F2P}$ and $H_{P2D}$ hold the same meaning as in Equation (3) and may be obtained in a similar way.

Region $R_3$ is the common region shared by regions $R_1$ and $R_2$. During the displacement of the focal point from the focal point 901 to the focal point 902, region $R_3$ may always be illuminated. The non-uniform ASG (not shown in FIG. 9) of the detector 950 may be configured so that at least a pair of first detector unit and second detector unit may locate within the region $R_3$. The signals generated by the first detector unit and the second detector unit may be extensively collected (e.g., 1~500 samples per second) during the displacement of the focal point between the focal points 901 and 902. A first intensity and a second intensity may be obtained by the correlation determination sub-module 344 at each of a plurality of predetermined time points. The correlation determination sub-module 344 may also determine a displacement from the focal point 901 to the current focal point at each of the plurality of predetermined time points (e.g., according to the exemplary method described above or in a similar manner). The correlation determination sub-module 344 may generate a correlation between a ratio of the first intensity to the second intensity and the displacement. The correlation may be in the form of one or more mathematical functions (e.g., by fitting), or a lookup table (e.g., by recording). The generated correlation may be stored in a storage device (e.g., storage 150, storage 220, storage 275, memory 280) for further use. In 820 of process 800 illustrated in FIG. 8, the focal point determination sub-module 342 may obtain the correlation from the storage device to determine the displacement of the focal points.

In some embodiments, the determination of the correlation may be performed during the acquisition of scan data by the CT scanner 110.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on at least one machine each of which has at least one processor and a storage device, the method comprising:
   determining a first intensity of first radiation incident on a first detector unit of a scanner, the scanner including a non-uniform anti-scatter grid (ASG) and a radiation source, the non-uniform ASG being configured according to a first focal point of the radiation source;
   determining a second intensity of second radiation incident on a second detector unit of the scanner, wherein the first radiation and the second radiation are emitted from the radiation source with a second focal point; and
   determining a reference radiation intensity for at least one of the first detector unit or the second detector unit;
   obtaining a first ratio of the first intensity to a first reference radiation intensity for the first detector unit;
   obtaining a second ratio of the second intensity to a second reference radiation intensity for the second detector unit:
   determining a direction of the displacement by comparing the first ratio and the second ratio; and
   determining a displacement of the second focal point from the first focal point based on the direction of the displacement.

2. The method of claim 1, further comprising:
   obtaining at least one parameter relating to the configuration of the ASG, wherein the at least one parameter includes a height of at least a portion of the non-uniform ASG, a width of the at least a portion of the non-uniform ASG, or a distance from the second focal point to the portion of the non-uniform ASG; and
   determining the displacement based on the at least one parameter.

3. The method of claim 2, wherein
   the non-uniform ASG includes at least one first cell, and
   the first detector unit and the second detector unit are included in the at least one first cell.

4. The method of claim 2, wherein
   the non-uniform ASG includes at least one second cell and at least one third cell,
   the at least one second cell and the at least one third cell include plates of different heights,
   the first detector unit is included in the at least one second cell, and
   the second detector unit is included in the at least one third cell.

5. The method of claim 1, wherein the reference radiation intensity for at least one of the first detector unit or the second detector unit corresponds to an intensity of the radiation received by the first detector unit or the second detector when a focal point of the radiation source is at the first focal point.

6. The method of claim 5, wherein the determining a reference radiation intensity for at least one of the first detector unit or the second detector unit comprising:
   obtaining a plurality of first intensities and second intensities at different time points;
   determine, as the time the ASG aligned with the first focal point, a time point when a sum of a first intensity and a second intensity reaches maximum among the different time points; and
   determining the first intensity and the second intensity at the determined time point as the reference radiation intensity for the first detector unit and the second detector respectively.

7. The method of claim 6, further comprising:
   determining an average of the first intensity and the second intensity at the determined time point as the reference radiation intensity for both of the first detector unit and the second detector.

8. The method of claim 7, the first radiation and the second radiation being emitted during the obtaining the scan data.

9. The method of claim 1, further comprising:
   generating, based on the displacement, a calibration instruction for calibrating the scanner.

10. The method of claim 1, further comprising:
    obtaining scan data by causing the scanner to scan a subject; and
    generating an image based on the scan data and the displacement.

11. A system, comprising at least one processor and at least one storage for storing instructions, the instructions, when executed by the at least one processor, causing the at least one processor to:
- determine a first intensity of first radiation incident on a first detector unit of a scanner, the scanner including a non-uniform anti-scatter grid (ASG) and a radiation source, the non-uniform ASG being configured according to a first focal point of the radiation source;
- determine a second intensity of second radiation incident on a second detector unit of the scanner, wherein the first radiation and the second radiation are emitted from the radiation source with a second focal point;
- obtain a reference radiation intensity for at least one of the first detector unit or the second detector unit;
- obtaining a first ratio of the first intensity to a first reference radiation intensity for the first detector unit;
- obtaining a second ratio of the second intensity to a second reference radiation intensity for the second detector unit:
- determining a direction of the displacement by comparing the first ratio and the second ratio; and
- determine a displacement of the second focal point from the first focal point based on the direction of the displacement.

12. The system of claim 11, the at least one processor is further configured to:
- obtain at least one parameter relating to the configuration of the ASG, wherein the at least one parameter includes a height of at least a portion of the non-uniform ASG, a width of the at least a portion of the non-uniform ASG, or a distance from the second focal point to the portion of the non-uniform ASG; and
- determine the displacement based on the at least one parameter.

13. The system of claim 12, wherein
the non-uniform ASG includes at least one first cell, and
the first detector unit and the second detector unit are included in the at least one first cell.

14. The system of claim 12, wherein
the non-uniform ASG includes at least one second cell and at least one third cell,
the at least one second cell and the at least one third cell includes plates of different heights,
the first detector unit is included in the at least one second cell, and
the second detector unit is included in the at least one third cell.

15. The system of claim 11, wherein the reference radiation intensity for at least one of the first detector unit or the second detector unit corresponds to an intensity of the radiation received by the first detector unit or the second detector when a focal point of the radiation source is at the first focal point.

16. The system of claim 15, wherein to obtain the reference radiation intensity for at least one of the first detector unit or the second detector unit, the at least one processor is configured to:
- obtain a plurality of first intensities of the at least one of the first detector unit and a plurality of second intensities of the at least one of the second detector unit at different time points;
- determine, as the time the ASG aligned with the first focal point, a time point when a sum of a first intensity and a second intensity reaches maximum among the different time points; and
- determine the first intensity and the second intensity at the determined time point as the reference radiation intensity for the at least one of the first detector unit and the at least one of the second detector respectively.

17. The system of claim 16, the at least one processor is further configured to
- determine an average of the first intensity and the second intensity at the determined time point as the reference radiation intensity for both of the first detector unit and the second detector.

18. The system of claim 11, the at least one processor is further configured to:
- generate, based on the displacement, a calibration instruction for calibrating the scanner.

19. The system of claim 11, the at least one processor is further configured to:
- obtain scan data by causing the scanner to scan a subject, and
- generate an image based on the scan data and the displacement.

20. A non-transitory computer readable medium, storing instructions, the instructions when executed by a processor, causing the processor to execute operations comprising:
- determining a first intensity of first radiation incident on a first detector unit of a scanner, the scanner including a non-uniform anti-scatter grid (ASG) and a radiation source, the non-uniform ASG being configured according to a first focal point of the radiation source;
- determining a second intensity of second radiation incident on a second detector unit of the scanner, wherein the first radiation and the second radiation are emitted from the radiation source with a second focal point;
- determining a reference radiation intensity for at least one of the first detector unit or the second detector unit;
- obtaining a first ratio of the first radiation intensity to a first reference radiation intensity for the first detector unit;
- obtaining a second ratio of the second radiation intensity to a second reference radiation intensity for the second detector unit; and
- determining a direction of the displacement by comparing the first ratio and the second ratio; and
- determining a displacement of the second focal point from the first focal point based on the direction of the displacement.

* * * * *